US007655433B2

(12) United States Patent
Aebersold

(10) Patent No.: US 7,655,433 B2
(45) Date of Patent: Feb. 2, 2010

(54) METHODS FOR HIGH-THROUGHPUT AND QUANTITATIVE PROTEOME ANALYSIS

(75) Inventor: Rudolf H. Aebersold, Mercer Island, WA (US)

(73) Assignee: The Institute for Systems Biology, Seattle, WA (US)

( * ) Notice: Subject to any disclaimer, the term of this patent is extended or adjusted under 35 U.S.C. 154(b) by 0 days.

(21) Appl. No.: 10/455,246

(22) Filed: Jun. 4, 2003

(65) Prior Publication Data

US 2004/0033625 A1    Feb. 19, 2004

Related U.S. Application Data

(60) Provisional application No. 60/385,941, filed on Jun. 4, 2002.

(51) Int. Cl.
| | | |
|---|---|---|
| C12Q 1/37 | (2006.01) | |
| C12Q 1/00 | (2006.01) | |
| C12Q 1/34 | (2006.01) | |
| C12N 9/48 | (2006.01) | |
| C12N 9/76 | (2006.01) | |
| C12P 19/30 | (2006.01) | |

(52) U.S. Cl. ............................. 435/23; 435/4; 435/18; 435/212; 436/89

(58) Field of Classification Search ........................ None
See application file for complete search history.

(56) References Cited

U.S. PATENT DOCUMENTS

| | | |
|---|---|---|
| 6,824,981 B2 | 11/2004 | Chait et al. |
| 2002/0146349 A1 | 10/2002 | Gygi et al. |
| 2003/0148462 A1 | 8/2003 | Kirschner et al. |
| 2004/0229283 A1 | 11/2004 | Gygi et al. |
| 2004/0235186 A1 | 11/2004 | Gygi et al. |
| 2004/0259164 A1 | 12/2004 | Gygi et al. |
| 2005/0164324 A1 | 7/2005 | Gygi |

FOREIGN PATENT DOCUMENTS

| | | |
|---|---|---|
| WO | WO00/11208 | 3/2000 |
| WO | WO 03/078962 A2 | 9/2003 |

OTHER PUBLICATIONS

Griffin et al. (2001). "Quantitative proteomic analysis using a MALDI quadrupole time-of-flight mass spectrometer," Analytical Chemistry vol. 73, pp. 978-986.*
J. Ji et al. (2000). "Strategy for qualitative and quantitative analysis in proteomics based on signiture peptides," Journal of Chromatography B vol. 745, pp. 197-210.*
W. Schroedl, L. Jaekel, and M. Krueger "C-Reactive Protein and Antibacterial Activity in Blood Plasma of Colostrum-Fed Calves and the Effect of Lactulose" J. Dairy Sci. 86:3313-3320 .*
Dictionary.com (www.dictionary.com), Definition of "synthetic" and "correspond" Last accessed May 17, 2006.*
Answers.com definition of "blood plasma" and "serum". Accessed May 17, 2006 4pgs.*
William Williams, David Weiner, "Biologically Active Peptides:Design, Synthesis and Utilization", 1993, CRC Press, p. 124 to 126.*
Stryer, Lubert, "Biochemistry" 4th ed., WH Freeman p. 56-57.*
Viaene et al. "Efficient expression of bovine a-lactalbumin in *Saccharomyces cerevisiae*" Eur. J. Biochem. 202, 471-477 (1991).*
Swiss-Prot, Uni-Prot knowledge database, (http://ca.expasy.org/sprot/) Accessed May 17, 2006.*
Yasushi Ishihama, Toshitaka Sato, Tsuyoshi Tabata, Norimasa Miyamoto, Koji Sagane, Takeshi Nagasu & Yoshiya Oda, Quantitative mouse brain proteomics using culture-derived isotope tags as internal standards, Nature Biotechnology 23, 617-621 (2005), Published online: Apr. 17, 2005.*
JR Barr, VL Maggio, DG Patterson Jr, GR Cooper, LO Henderson, WE Turner, SJ Smith, WH Hannon, LL Needham and EJ Sampson, Isotope dilution—mass spectrometric quantification of specific proteins: model application with apolipoprotein A-I, Clinical Chemistry, vol. 42, 1676-1682, (1996).*
David R. Barnidge, Edward A. Dratz, Therese Martin, Leo E. Bonilla, Liam B. Moran, and Arnold Lindall , Absolute Quantification of the G Protein-Coupled Receptor Rhodopsin by LC/MS/MS Using Proteolysis Product Peptides and Synthetic Peptide Standards, Analytical chemistry, 75(3), pp. 445-451 (2003).*
Lambert, J.B., Shurvell, H.F, Lightner, D.A., and Cooks, R.G. "Basics of Mass Spectrometry" Introduction to Organic Spectroscopy. MacMillan, 1987, chapter 11, pp. 315-344.*
Dictionary.com (www.dictionary.com), Definition of "synthetic" and "correspond" , Last accessed May 17, 2006, 7 pages.*
Answers.com definition of "blood plasma" and "serum", Accessed May 17, 2006, 4 pages.*
William Williams, David Weiner, "Biologically Active Peptides:Design, Synthesis and Utilization", CRC Press, 1993, pp. 124 to 126.*
Stryer, Lubert, "Biochemistry" 4th ed., WH Freeman, 1995, pp. 56-57.*
Viaene, et al. "Efficient expression of bovine a-lactalbumin in *Saccharomyces cerevisiae*" Eur. J. Biochem., 1991, vol. 202, pp. 471-477.*

(Continued)

*Primary Examiner*—Christopher R Tate
*Assistant Examiner*—Aaron J Kosar
(74) *Attorney, Agent, or Firm*—McDermott Will & Emery LLP

(57) ABSTRACT

The invention provides methods for identifying and quantifying polypeptides in a sample. The methods include the steps of labeling peptides in a polypeptide sample with an isotope tag; adding a plurality of peptide standards to the polypeptide sample, wherein the peptide standards are labeled with an isotopically distinct version of the isotope tag; resolving the labeled sample and standard peptides into a plurality of fractions; analyzing the resolved fractions using mass spectrometry; identifying an isotope-tagged sample peptide in an analyzed fraction; and determining the amount of the identified isotope-tagged sample peptide in the analyzed fraction by comparison to the amount of isotope tagged standard peptide in the same fraction.

30 Claims, 9 Drawing Sheets

Swiss-Prot, Uni-Prot knowledge database, (http://ca.expasy.org/sprot/) Accessed May 30, 2006, 3 pages.*

Yasushi Ishihama, Toshitaka Sato, Tsuyoshi Tabata, Norimasa Miyamoto, Koji Sagane, Takeshi Nagasu & Yoshiya Oda, "Quantitative mouse brain proteomics using culture-derived isotope tags as internal standards, Nature Biotechnology", 2005 (Published online: Apr. 17, 2005), vol. 23, pp. 617-621.*

JR Barr, VL Maggio, DG Patterson Jr, GR Cooper, LO Henderson, WE Turner, SJ Smith, WH Hannon, LL Needham and EJ Sampson, "Isotope dilution—mass spectrometric quantification of specific proteins: model application with apolipoprotein A-I", Clinical Chemistry, 1996, vol. 42, pp. 1676-1682.*

David R. Barnidge, Edward A. Dratz, Therese Martin, Leo E. Bonilla, Liam B. Moran, and Arnold Lindell, "Absolute Quantification of the G Protein-Coupled Receptor Rhodopsin by LC//MS/MS Using Proteolysis Product Peptides and Synthetic Peptide Standards", Analytical chemistry, 2003, 75(3), pp. 445-451.*

Aebersold and Goodlett, "Mass Spectrometry in Proteomics," *Chem. Rev.* 101: 269-295 (2001).

Aebersold and Mann, "Mass spectrometry-based proteomics," *Nature* 422:198-207 (2003).

Bodansky and Bodansky, *The Practice of Peptide Synthesis*, vol. 21 Springer-Verlag, New York (1984).

Eng et al., "An Approach to Correlate Tandem Mass Spectral Data of Peptides with Amino Acid Sequences in a Protein Database," *J. Amer. Soc. Mass Spec.* 5:976-989 (1994).

Gerber et al., Absolute quantification of proteins and phosphoproteins from cell lysates by tandem MS., *Proc. Natl. Acad. Sci. USA* 100:6940-6945 (2003).

Glazer et al., "Laboratory Techniques in Biochemistry and Molecular Biology: Chemical Modification of Proteins," *Elsevier Biomedical* chapter 3, pp. 68-120 (1975).

Goshe et al., "Phosphoprotein Isotope-Coded Affinity Tag Approach for Isolating and Quantitating Phosphopeptides in Proteome-Wide Analyses," *Anal. Chem.* 73:2578-2586 (2001).

Griffin and Aebersold, "Advances in Proteome Analysis by Mass Spectrometry," *J. Biol. Chem.* 276:45497-45500 (2001).

Gygi et al., "Quantitative analysis of complex protein mixtures using isotope-coded affinity tags," *Nature Biotechnical* 17:994-999 (1999).

Hermanson, "Bioconjugate Techniques," *Academic Press* pp. 297-364 (1996).

Houghten, R., "General method of the rapid solid-phase synthesis of large numbers of peptides: specificity of antigen-antibody interaction at the level of individual amino acids," *Proc. Natl. Acad. Sci. USA*, 82:5131-5135 (1985).

Kinter and Sherman, "Protein Sequencing and Identification Using Tandem Mass Spectrometry," *John Wiley & Sons* (2000).

Merrifield, R.B., "Solid Phase Peptide Synthesis," *J. Am. Chem. Soc.* 85:2149-2154 (1963).

Smolka et al., "Optimization of the Isotope-Coded Affinity Tag-Labeling Procedure for Quantitative Proteome Analysis," *Anal. Chem.* 297:25-31 (2001).

Smolka et al., "Quantitative Protein Profiling Using Two-dimensional Gel Electrophoresis, Isotope-coded Affinity Tag Labeling, and Mass Spectrometry," *Molec. Cell. Proteomics* 1:19-29 (2002).

Yates et al., "Mass Spectrometry and the Age of the Proteome," *J. Mass Spect.* 33:1-19 (1998).

Zhou et al., "A systematic approach to the analysis of protein phosphorylation," *Nat. Biotechnol* 19:375-378 (2001).

Zhou et al., "Quantitative proteome analysis by solid-phase isotope tagging and mass spectrometry," *Nat. Biotechnol* 20:512-515 (2002).

Gerber et al., "Absolute quantification of proteins and phosphoproteins from cell lysates by tandem MS," *Proc. Natl. Acad. Sci. USA* 100: 6940-6945 (2003).

Harvard University, "Absolute Quantification of Proteins (AQUA)," http://www.techtransfer.harvard.edu/cgi-bin/TALSearch.cgi?full_report=1&case=1918>, 2006, 1 page.

Sigma-Aldrich, "AQUA Peptids",<http://www.sigmaaldrich.com/Area_of_Interest/Life_Science/Proteomics_and_Protein_Expr/Protein_Analysis/Mass_Spectrometry/Protein_AQUA.html>, 2006, 3 pages.

* cited by examiner

- Each array element contains "expected" and "unexpected" peptides
- The "expected" peptides are identified as paired signals

SEQUENCE LISTING

```
<160> NUMBER OF SEQ ID NOS: 2

<210> SEQ ID NO 1
<211> LENGTH: 9
<212> TYPE: PRT
<213> ORGANISM: Homo sapiens

<400> SEQUENCE: 1

Gly Ser Asp Phe Asp Cys Glu Leu Arg
1               5

<210> SEQ ID NO 2
<211> LENGTH: 17
<212> TYPE: PRT
<213> ORGANISM: Homo sapiens
```

-continued

```
<400> SEQUENCE: 2

Arg Pro Ser Ala Asn Cys Asp Pro Phe Ser Val Thr Glu Ala Leu Ile
1               5                   10                  15
Arg
```

METHODS FOR HIGH-THROUGHPUT AND QUANTITATIVE PROTEOME ANALYSIS

This application claims the benefit of priority of U.S. Provisional application Ser. No. 60/385,941 filed Jun. 4, 2002, the entire contents of which is incorporated herein by reference.

This invention was made with government support under grant number CA 84698 awarded by the National Cancer Institute. The government has certain rights in the invention.

BACKGROUND OF THE INVENTION

The present invention relates generally to proteomics and more specifically to quantitative proteomics analysis.

Complete genomic sequences and large partial (EST) sequence databases can potentially allow the identification of every gene in a species. However, the sequences alone do not explain the mechanism of biological and clinical processes because neither the amount nor the activity of the protein products can be easily predicted from the gene sequence. From genomic analysis or the analysis of the expressed mRNA transcripts, neither the quantity nor the structure, activity and state of modification of the translated protein products can be predicted. Furthermore, the gene sequence alone cannot be used to reliably predict whether and how a gene will be spliced and how and at what position a protein is modified.

In order to assess the physiological state of a cell or organism using proteomics, it is important to understand the nature of protein modifications and the quantities of expressed proteins. As biological systems are dynamic, such technologies need to be quantitative. Such an analysis requires methods for the determination of the absolute quantity of each protein in a biological or clinical sample and for the determination of the precise composition of the proteins. This includes the determination of splice forms and modifications.

A number of approaches have been used to address the needs of proteomics analysis. For example, the combination of two-dimensional gel electrophoresis (2DE) and protein identification by mass spectrometry (MS) or tandem MS (MS/MS) constitute such a method. However, a limitation to this approach is that 2DE-MS analysis does not provide a true representation of the proteins in a biological sample because specific classes of proteins are known to be absent or under represented in 2D gel patterns. These include very acidic or basic proteins, excessively large or small proteins, membrane proteins and other proteins of poor solubility in aqueous solvents, and low abundance proteins.

Other methods for proteome analysis include quantitative mass spectrometry based on multidimensional peptide separation and isotope coded affinity tagging of proteins. This method allows relative quantitation, that is, the determination of the abundance ratio of each protein in two samples but does not allow determination of the absolute quantity of the proteins in a sample. Also, chip technology using arrays of reagents with known specificity for target proteins such as antibody arrays or arrays of aptamers can be used for proteomics analysis. However, the use of such arrays can be limited by the need to selectively capture representative proteins or preserve the three dimensional structure of the proteins depending on the particular use of the chip.

Mass spectrometry (MS) based methods for proteomics have in common that the currency of protein identification and quantification is a peptide generated by the sequence specific fragmentation of a protein. Therefore, proteins need to be enzymatically or chemically fragmented prior to mass spectrometric analysis. Furthermore, the MS based proteomic methods, alone or in conjunction with other methods, have in common that throughput is limited by the need to sequence each peptide in each sample in each experiment to determine the sequence identity of the protein analyzed. A protein generally generates a large number of peptides and hence a large number of peptides has to be sequenced per experiment. The yeast proteome is estimated to contain approximately 6000 open reading frames (ORF's), which would generate approximately 300,000 to 400,000 tryptic peptides, depending on how specifically the enzyme works to cleave the yeast proteins. Thus, a huge number of peptides would need to be analyzed for determination of the physiological state in a sample, even if only a subset of all possible genes is expressed in a cell at a given state.

Thus, there exists a need for methods of high throughput and quantitative proteome analysis. The present invention satisfies this need and provides related advantages as well.

SUMMARY OF THE INVENTION

The invention provides methods for identifying and quantifying polypeptides in a sample. The methods include the steps of labeling peptides in a polypeptide sample with an isotope tag; adding a plurality of peptide standards to the polypeptide sample, wherein the peptide standards are labeled with an isotopically distinct version of the isotope tag; resolving the labeled sample and standard peptides into a plurality of fractions; analyzing the resolved fractions using mass spectrometry; identifying an isotope-tagged sample peptide in an analyzed fraction; and determining the amount of the identified isotope-tagged sample peptide in the analyzed fraction by comparison to the amount of isotope tagged standard peptide in the same fraction.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7A shows a schematic representation of the fourplexed RP-µLC system. The system components can be segmented into four modules: sample loading, solvent delivery, separation, and fractionation. FIG. 7B shows the flow-path and valve configurations at the injection stage of the fourplexed RP-µLC system. FIG. 7C shows the flow-path and valve configurations at the separation stage of the fourplexed RP-µLC system.

DETAILED DESCRIPTION OF THE INVENTION

Figure 1:
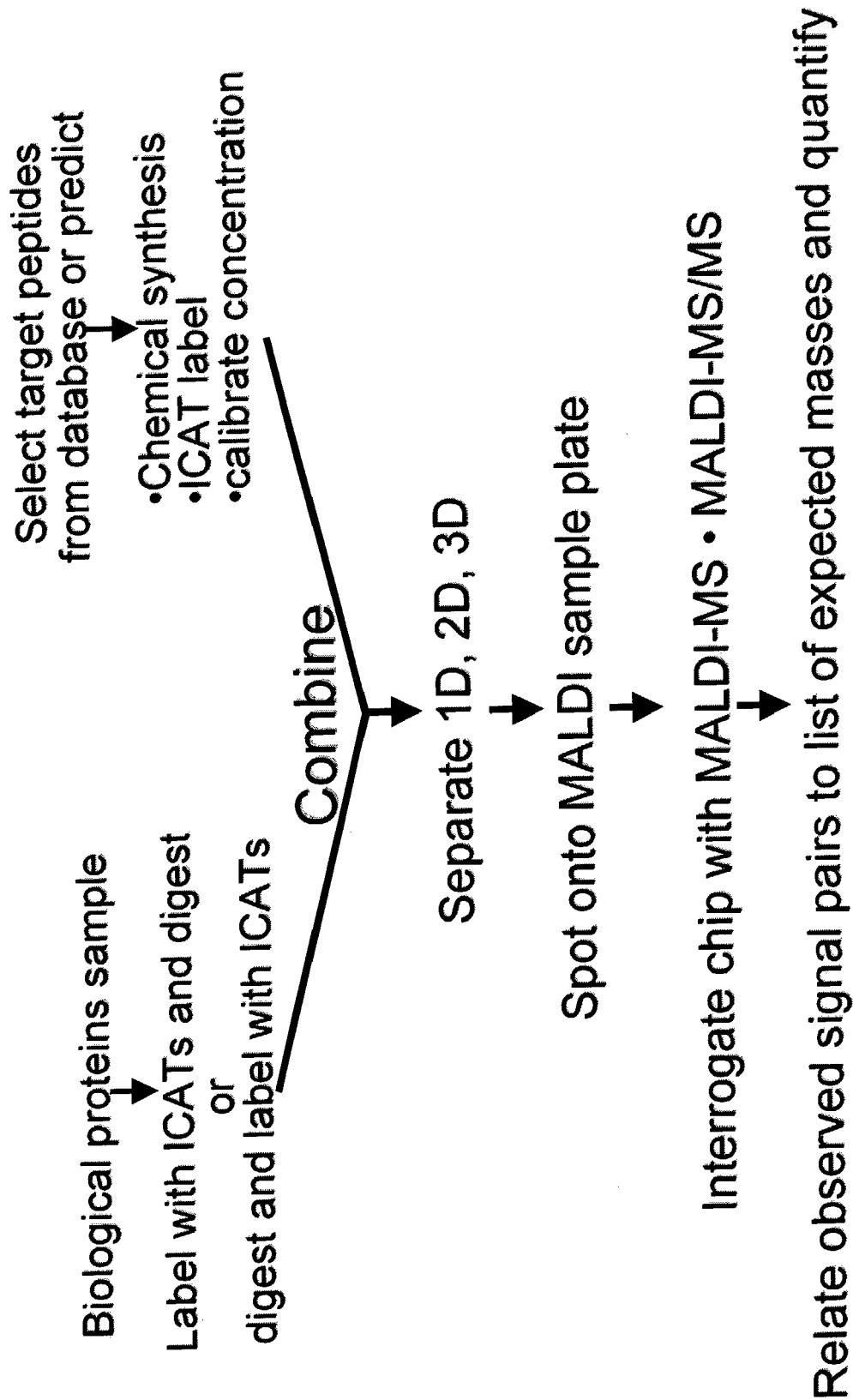
FIG. 1 shows a flow chart for the generation of ordered peptide arrays for quantitative protein profiling using calibrated synthetic external standard peptides. Sample and standard peptides are isotopically labeled, combined, and analyzed by mass spectrometry (MS).

The invention provides methods to determine the absolute quantity of proteins present in a biological sample rapidly and in an automated manner. The methods can be used to detect and quantify splicing and other isoforms as well as specific modifications of sample polypeptides. The methods are based on generating an ordered array of differentially isotopically tagged pairs of peptides, each pair representing a unique protein, a specific protein isoform, or a specifically modified form of a protein. One element of the peptide pairs is a synthetically generated, external standard and the other element of the pair is a peptide generated by enzymatic digestion of the proteins in the sample mixture. The peptide array is generated by separating the peptide mixtures via a sequence of reproducible separation steps and depositing the final peptide fractions on the sample plate of a MALDI mass spectrometer. The peptide array is then interrogated by a mass spectrometer to identify the proteins present in a biological or clinical sample and to determine the absolute abundance of each. The position on the array, which reflects the separation coordinates of the separation systems used, in conjunction with the precise mass measurement of the peptide, uniquely identifies each peptide and therefore the protein it represents. The methods can be used to build on the availability of whole genome sequences, of software tools for the prediction of open reading frames (ORF)'s, splice isoforms, modification sites and also on the large amount of experimental data that are being accumulated by large scale protein measuring projects.

The methods of the invention essentially change a mass spectrometry based quantitative proteomics experiment from a shotgun sequencing approach, in which in every experiment each detected peptide is sequenced by MS/MS, into a targeted interrogation of the sample, in which the presence and quantity of a predetermined set of peptides is determined. The methods of the invention can include the following steps: generation of isotope tagged, calibrated peptide samples; preparation and isotope tagging of protein sample; generation of the ordered peptide array; interrogation of the ordered array by mass spectrometry or tandem mass spectrometry; and data analysis and display.

In one embodiment, the invention provides a method for identifying and/or quantifying polypeptides in a sample. The method can include the steps of labeling polypeptides in a polypeptide sample with an isotope tag; adding a plurality of peptide standards to the polypeptide sample, wherein the peptide standards are labeled with an isotopically distinct version of the isotope tag; resolving the labeled sample and standard peptides into a plurality of fractions; analyzing the resolved fractions using mass spectrometry; identifying an isotope-tagged sample peptide in an analyzed fraction; and determining the amount of the identified isotope-tagged sample peptide in the analyzed fraction by comparison to the amount of isotope tagged standard peptide in the same fraction.

An exemplary embodiment of the invention is shown in FIG. 1. A set of target peptides is selected from a database or predicted from known sequences. A set of target peptides is synthesized that would correspond to a predetermined fragmentation of parent polypeptides, for example, digestion with a protease or chemical cleavage, and labeled with an isotope tag, here illustrated as an ICAT™ label. The standard peptides are calibrated so that absolute amounts are known and added for comparison and quantification. A sample of interest, such as a biological sample, is also labeled with the same isotope tag as used for the standard peptides except differing in the isotopic label. Polypeptides in the sample are digested with a protease or chemically cleaved in the same manner as for the selected target peptides. The sample and standard peptides are combined and resolved in parallel using one or more fractionation techniques, for example, 1, 2 or 3 dimensional modes of separation. The fractions are spotted on a MALDI sample plate. The arrayed fractions are interrogated with MALDI-MS and/or MALDI-MS/MS. Paired signals corresponding to differentially labeled sample and standard peptides are observed and related to a list of expected masses based on the particular standard peptides included. The addition of known amounts of standard peptides also allows for quantification of the corresponding sample peptides.

The methods of the invention are useful for proteome analysis and can be used to identify and quantify multiple polypeptides in a complex sample. The methods can be used, for example, for blood serum profiling, clinical applications, analysis of the physiological state of a biological sample, splice isoform mapping and profiling, and mapping and profiling of post-translational modifications.

As used herein, the term "polypeptide" refers to a peptide or polypeptide of two or more amino acids. A polypeptide can also be modified by naturally occurring modifications such as post-translational modifications, including phosphorylation, fatty acylation, prenylation, sulfation, hydroxylation, acetylation, addition of carbohydrate, addition of prosthetic groups or cofactors, formation of disulfide bonds, proteolysis, assembly into macromolecular complexes, and the like.

As used herein, the term "sample" is intended to mean any biological fluid, cell, tissue, organ or portion thereof, that includes one or more different molecules such as nucleic acids, polypeptides, or small molecules. A sample can be a tissue section obtained by biopsy, or cells that are placed in or adapted to tissue culture. A sample can also be a biological fluid specimen such as blood or plasma, cerebrospinal fluid, urine, saliva, seminal plasma, pancreatic juice, and the like. A sample can additionally be a cell extract from any species, including prokaryotic and eukaryotic cells as well as viruses. A tissue or biological fluid specimen can be further fractionated, if desired, to a fraction containing particular cell types.

As used herein, a "polypeptide sample" refers to a sample containing two or more different polypeptides. A polypeptide sample can include tens, hundreds, or even thousands or more different polypeptides. A polypeptide sample can also include non-protein molecules so long as the sample contains polypeptides. A polypeptide sample can be a whole cell or tissue extract or can be a biological fluid. Furthermore, a polypeptide sample can be fractionated using well known methods, as disclosed herein, into partially or substantially purified protein fractions.

The use of biological fluids such as a body fluid as a sample source is particularly useful in methods of the invention. Biological fluid specimens are generally readily accessible and available in relatively large quantities for clinical analysis. Biological fluids can be used to analyze diagnostic and prognostic markers for various diseases. In addition to ready accessibility, body fluid specimens do not require any prior knowledge of the specific organ or the specific site in an organ that might be affected by disease. Because body fluids, in particular blood, are in contact with numerous body organs, body fluids "pick up" molecular signatures indicating pathology due to secretion or cell lysis associated with a pathological condition.

The methods of the invention are based on the identification of distinct peptides which are unique for a polypeptide and can therefore be used to identify the presence and quantity of the polypeptide in a sample. Peptides uniquely identifying a protein can be selected experimentally or computationally. Experimentally such peptides are selected from databases that contain all the peptides from a species that have been previously observed, for example, in tandem mass spectrometry experiments. Computationally such peptides are selected by translating the complete genomic sequence or the sequence of all predicted genes and their splice forms into the corresponding amino acid sequences, by applying the rules for cleavage that are predictable with each chemical or enzymatic protein cleavage reagent to these amino acid sequence, and by computing the sequence, mass and other properties for each of the generated peptides. From this database of predicted peptides, a suitable selection of peptides that are unique for each target protein is then selected.

Once a set of peptides is selected, the selected set of standard peptides can be made by synthesizing a peptide unique for a polypeptide and tagging the standard peptide in a manner that allows identification and quantification of the same unique is peptide derived from a sample polypeptide. The tagging is carried out so that differential isotope tags can be separately added to the standard peptides and the sample peptides. The tagged standard and sample peptides are co-purified and analyzed by mass spectrometry so that the isotope tagged peptides can be identified. Due to the fact that the standard peptide and the peptide derived from the sample are chemically identical but isotopically distinguished, they co-purify in the separation methods used. The addition of a known amount of the standard therefore allows direct comparison and determination of the amount of the corresponding sample peptide.

The sample proteins are labeled with a chemically identical but isotopically different tagging reagent to the one used to generate the standard peptide mixtures. The tagged protein sample is digested using the protease that was planned in the design of the standard peptides.

As used herein an "isotope tag" refers to a chemical moiety having suitable chemical properties for incorporation of an isotope, allowing the generation of differentially labeled reagents which can be used to differentially tag a polypeptide in two samples. The isotope tag also has an appropriate composition to allow incorporation of a stable isotope at one or more atoms. A particularly useful stable isotope pair is hydrogen and deuterium, which can be readily distinguished using mass spectrometry as light and heavy forms, respectively. Any of a number of isotopic atoms can be incorporated into the isotope tag so long as the heavy and light forms can be distinguished using mass spectrometry, for example, $^{13}C$, $^{15}N$, $^{17}O$, $^{18}O$ or $^{34}S$. Exemplary isotope tags include the 4,7,10-trioxa-1,13-tridecanediamine based linker and its related deuterated form, 2,2',3,3',11,11',12,12'-octadeutero-4,7,10-trioxa-1,13-tridecanediamine, described by Gygi et al. (*Nature Biotechnol.* 17:994-999 (1999). Other exemplary isotope tags have also been described previously (see WO 00/11208, which is incorporated herein by reference). In contrast to these previously described isotope tags related to an ICAT-type reagent, it is not required that an affinity tag be included in the reagent since the polypeptides are already isolated. One skilled in the art can readily determine any of a number of appropriate isotope tags useful in methods of the invention.

Thus, an isotope tag can be an alkyl, akenyl, alkynyl, alkoxy, aryl, and the like, and can be optionally substituted, for example, with O, S, N, and the like, and can contain an amine, carboxyl, sulfhydryl, and the like (see WO 00/11208). These and other derivatives can be made in the same manner as that disclosed herein using methods well known to those skilled in the art. One skilled in the art will readily recognize that a number of suitable chemical groups can be used as an isotope tag so long as the isotope tag can be differentially isotopically labeled. The stable isotope tag can also be introduced via a solid-phase stable isotope tag transfer method, such as the one described by Zhou et al., *Nature Biotechnol.* 20:512-515 (2002).

The peptide fragments are tagged with an isotope tag to facilitate MS analysis. In order to tag the peptide fragments, the isotope tag contains a reactive group that can react with a chemical group on the peptide portion of the peptide fragments. A reactive group is reactive with and therefore can be covalently coupled to a molecule in a sample such as a polypeptide. Reactive groups are well known to those skilled in the art (see, for example, Hermanson, *Bioconjugate Techniques*, pp. 297-364, Academic Press, San Diego (1996); Glazer et al., *Laboratory Techniques in Biochemistry and Molecular Biology: Chemical Modification of Proteins*, Chapter 3, pp. 68-120, Elsevier Biomedical Press, New York (1975); Pierce Catalog (1994), Pierce, Rockford Ill.). Any of a variety of reactive groups can be incorporated into an isotope tag for use in methods of the invention so long as the reactive group can be covalently coupled to a polypeptide or other desired molecule in a sample. For example, a polypeptide can be coupled via a sulfhydryl reactive.group, which can react with free sulfhydryls of cysteine or reduced cystines in a polypeptide. An exemplary sulfhydryl reactive group includes an iodoacetamido group (see Gygi et al., supra, 1999). Other examplary sulfhydryl reactive groups include maleimides, alkyl and aryl halides, haloacetyls, α-haloacyls, pyridyl disulfides, aziridines, acrylolyls, arylating agents and thiomethylsulfones.

A reactive group can also react with amines such as the α-amino group of a peptide or the ε-amino group of the side chain of Lys, for example, imidoesters, N-hydroxysuccinimidyl esters (NHS), isothiocyanates, isocyanates, acyl azides, sulfonyl chlorides, aldehydes, ketones, glyoxals, epoxides (oxiranes), carbonates, arylating agents, carbodiimides, anhydrides, and the like. A reactive group can also react with carboxyl groups found in Asp or Glu or the C-terminus of a peptide, for example, diazoalkanes, diazoacetyls, carbonyl-diimidazole, carbodiimides, and the like. A reactive group that reacts with a hydroxyl group includes, for example, epoxides, oxiranes, carbonyldiimidazoles, N,N'-disuccinimidyl carbonates, N-hydroxycuccinimidyl chloroformates, and the like. A reactive group can also react with amino acids such as histidine, for example, α-haloacids and amides; tyrosine, for example, nitration and iodination; arginine, for example, butanedione, phenylglyoxal, and nitromalondialdehyde; methionine, for example, iodoacetic acid and iodoacetamide; and tryptophan, for example, 2-(2-nitrophenylsulfenyl)-3-methyl-3-bromoindolenine (BNPS-skatole), N-bromosuccinimide, formylation, and sulfenylation (Glazer et al., supra, 1975). In addition, a reactive group can also react with a phosphate group for selective labeling of phosphopeptides (Zhou et al., *Nat. Biotechnol.*, 19:375-378 (2001)), or with other covalently modified peptides, including lipopeptides, or any of the known covalent polypeptide modifications. One skilled in the art can readily determine conditions for modifying sample molecules by using various reagents, incubation conditions and time of incubation to obtain conditions optimal for modification of molecule with an isotope tag. The use of covalent-chemistry based isolation methods is particularly useful due to the highly specific nature of the binding of the polypeptides.

The reactive groups described above can form a covalent bond with the target sample molecule. However, it is understood that an isotope tag can contain a reactive group that can non-covalently interact with a sample molecule so long as the interaction has high specificity and affinity.

A particularly useful method for labeling sample polypeptides is the use of the isotope-coded affinity tag (ICAT™) method (Gygi et al., *Nature Biotechnol.* 17:994-999 (1999); WO 00/11208; each of which is incorporated herein by reference). The labeling procedures are essentially the same as developed for ICAT reagent protein labeling. The ICAT™ type reagent method uses an affinity tag that can be differentially labeled with an isotope that is readily distinguished using mass spectrometry. The ICAT™ type affinity reagent consists of three elements, an affinity tag, a linker and a reactive group.

One element of the ICAT™ type affinity reagent is an affinity tag that allows isolation of peptides coupled to the affinity reagent by binding to a cognate binding partner of the affinity tag. A particularly useful affinity tag is biotin, which binds with high affinity to its cognate binding partner avidin, or related molecules such as streptavidin, and is therefore stable to further biochemical manipulations. Any affinity tag can be used so long as it provides sufficient binding affinity to its cognate binding partner to allow isolation of peptides coupled to the ICAT™ type affinity reagent. An affinity tag can also be used to isolate a tagged peptide with magnetic beads or other magnetic format suitable to isolate a magnetic affinity tag. In the ICAT™ type reagent method, or any other method of affinity tagging a peptide, the use of covalent trapping can be used to bind the tagged peptides to a solid support, if desired.

A second element of the ICAT™ type affinity reagent is a linker that can incorporate a stable isotope. The linker has a sufficient length to allow the reactive group to bind to a specimen polypeptide and the affinity tag to bind to its cognate binding partner. The linker also has an appropriate composition to allow incorporation of a stable isotope at one or more atoms. A particularly useful stable isotope pair is hydrogen and deuterium, which can be readily distinguished using mass spectrometry as light and heavy forms, respectively. Any of a number of isotopic atoms can be incorporated into the linker so long as the heavy and light forms can be distinguished using mass spectrometry. Exemplary linkers include the 4,7,10-trioxa-1,13-tridecanediamine based linker and its related deuterated form, 2,2',3,3',11,11',12,12'-octadeutero-4,7,10-trioxa-1,13-tridecanediamine, described by Gygi et al. (supra, 1999). One skilled in the art can readily determine any of a number of appropriate linkers useful in an ICAT™ type affinity reagent that satisfy the above-described criteria, as described above for the isotope tag.

The third element of the ICAT™ type affinity reagent is a reactive group, which can be covalently coupled to a polypeptide in a specimen. Various reactive groups have been described above with respect to the isotope tag and can similarly be incorporated into an ICAT-type reagent.

The ICAT™ method or other similar methods can be applied to the analysis of the peptide fragments. The method generally involves the steps of automated tandem mass spectrometry and sequence database searching for peptide/protein identification; stable isotope tagging for quantification by mass spectrometry based on stable isotope dilution theory; and the use of specific chemical reactions for the selective isolation of specific peptides. For example, the previously described ICAT™ reagent contained a sulfhydryl reactive group, and therefore an ICAT™-type reagent can be used to label cysteine-containing peptide fragments released from the solid support. Other reactive groups, as described above, can also be used.

In addition to using isotope tags, other types of tags can be used as long as the tags allow differential labeling of calibrated standard peptides and sample-derived peptides. For example, fluorescent dyes that have the same mobility in the various fractionation steps but different spectral properties can be used. Similarly, other types of detectable tags, such as chromophores or radioisotopes, can be used. One skilled in the art can readily determine appropriate detectable labels to differentially label calibrated peptides and sample peptides so long as the fractionation steps used in methods of the invention provide sufficient separation space to separate the target peptides.

If desired, sample molecules can be modified, either before or after a fractionation step. For example, the methods of the invention are particularly useful for mass spectrometry (MS) analysis. In the case of MS analysis of polypeptides, it is often useful to cleave the polypeptide into smaller fragments, for example, by proteolysis. Thus, a polypeptide molecule can be enzymatically cleaved with one or more proteases into peptide fragments. Exemplary proteases useful for cleaving polypeptides include trypsin, chymotrypsin, pepsin, papain, *Staphylococcus aureus* (V8) protease, Submaxillaris protease, bromelain, thermolysin, and the like. Polypeptides can also be cleaved chemically, for example, using CNBr, acid or other chemical reagents.

For polypeptide fragmentation, the polypeptides in the sample mixture, or the polypeptides contained in each fraction if optional sample fractionation is employed, can be subjected to specific cleavage, for example, by trypsin. The use of sequence specific cleavage can be particularly useful because the termini of peptides cleaved by a sequence specific method can act as a constraint. However, it is understood that the cleavage method used to generate fragments need not be sequence specific, if desired.

Furthermore, for polypeptide tagging, the polypeptides in the sample can be denatured and optionally reduced. Reducing the sample can be particularly useful when the reactive group on the tagging reagent is reactive with a thiol. Other useful reactive groups include amino or carboxyl groups of polypeptides or specific post-translational modifications, including phosphate, carbohydrate or lipid.

For generation of standard peptides, a collection of peptides are synthesized. These peptides constitute the full space of proteome interrogation to performed in a particular experiment. Each peptide in the collection uniquely identifies a protein, a protein isoform or a specifically modified form of a protein. The sequence of the peptides is derived either from empirical determinations, for example, MS/MS experiments in which the peptide in question has been observed, or by the application of computer programs that select a set of peptides, including an optimal set of peptides for a particular application. The computer programs use the information contained in large protein identification datasets, for example, which peptides have been observed, genome sequences, with defined ORFs, splice isoform databases, and the like, to select one to a few peptides from each protein that uniquely identifies the protein, a protein isoform or a specific modification. Further important criteria for peptide selection are the peptide mass, which needs to be within the useful mass range of a mass spectrometer. Also, desirable properties of the selected peptides include solubility and physico-chemical features that allow common peptide separation methods to separate the peptides over a wide separation space. The peptides can also contain one or several chemical groups that can be targeted by isotope tagging reagents. In general, peptides containing rare amino acids, such as Cys, Met, and Trp, are selected so that the sample complexity can be minimized by the selective isolation of the peptides containing that amino acid.

The peptide standards can be selected to represent most or essentially all of the known polypeptides in a sample. Alternatively, a subset of polypeptides can be selected. For example, if a particular set of polypeptides is desired to be analyzed, then standard peptides are selected from this set of polypeptides rather than from other polypeptides known to be in the sample. This can be particularly useful for diagnostic applications in which particular diagnostic markers are to be analyzed rather than a complete proteomics analysis of the sample. The amount of standard peptides to be added can be adjusted, as desired, to facilitate quantification, and each of the peptide standards added need not be in the same amounts.

The peptide sequences, once selected, are chemically synthesized by solid-phase stepwise synthesis, stable isotope tagged and quantified. Methods of synthesizing peptides are well known to those skilled in the art (Merrifield, *J. Am. Chem. Soc.* 85:2149 (1964); Bodanszky, M., *Principles of Peptide Synthesis* (Springer-Verlag, 1984); Houghten, *Proc. Natl. Acad. Sci., USA* 82:5131 (1985)). For each peptide, a calibrated sample stock solution is prepared and stored. Quantification of the calibrated stock solution can be carried out by amino acid composition analysis, can be based on UV absorbance measurement or other spectrometric methods, or by weighing the dried peptide. The synthesized peptides can be isotopically tagged by reacting the standard peptides with an isotope tag, as described herein. Although isotope tagging is generally carried out in the same manner as the isotope tagging of the sample molecules, it is understood that the isotope tagging of the peptide standards can be synthesized at the time of synthesis of the peptide standards so long as the resulting isotope tagged standard peptides differ from the corresponding isotope tagged sample peptides only by the differential label of the isotope tag.

Alternatively, the standard peptides can be generated by expression in a genetically engineered organism such as *Escherichia coli* or other microorganisms. Each peptide can be expressed separately as a peptide product, as part of a larger polypeptide from which the peptide will be cut out by proteolysis, or in the form of concatenated peptides, which can be resolved into individual peptide species by proteolysis or chemical cleavage at suitable sites. Once isolated, the peptides generated by genetic engineering and overexpression are isotopically labeled and used in the methods of the invention, as with the chemically synthesized peptides.

For preparation of the protein samples, standard protocols are used to prepare and process the protein samples. Methods for preparing and processing protein samples are well known to those skilled in the art (Scopes, *Protein Purification: Principles and Practice*, third edition, Springer-Verlag, New York (1993)). If desired, the sample can be fractionated by a number of known fractionation techniques. Fractionation techniques can be applied at any of a number of suitable points in the methods of the invention. Thus, if desired, a substantially purified sample fraction can be used. One skilled in the art can readily determine appropriate steps for fractionating sample molecules based on the needs of the particular application of methods of the invention.

If desired, the sample can be fractionated by a number of known fractionation techniques. Since such fractionation methods separate molecules, such techniques are used to resolve sample molecules. As used herein, resolve, when used in reference to a polypeptide or peptide, refers to the process of separating a polypeptide or peptide from one or more other polypeptides or peptides. Methods for resolving sample molecules are well known to those skilled in the art. Fractionation methods, which can be used to resolve sample molecules, include but are not limited to subcellular fractionation or chromatographic techniques such as ion exchange, including strong and weak anion and cation exchange resins, hydrophobic and reverse phase, size exclusion, affinity, hydrophobic charge-induction chromatography, dye-binding, and the like (Ausubel et al., supra, 1999; Scopes, *Protein Purification: Principles and Practice*, third edition, Springer-Verlag, New York (1993); Burton and Harding, *J. Chromatogr. A* 814:71-81 (1998)). Other fractionation methods include, for example, centrifugation, electrophoresis, the use of salts, and the like (see Scopes, supra, 1993). One skilled in the art will recognize that these and other fractionation methods, which are well known to those skilled in the art, can be used to resolve polypeptides or peptides.

Affinity chromatography can also be used including, for example, dye-binding resins such as Cibacron blue, substrate analogs, including analogs of cofactors such as ATP, NAD, and the like, ligands, specific antibodies useful for immunoaffinity isolation, either polyclonal or monoclonal, and the like. Affinity chromatography can also be performed using DNA, lectins or other natural substances as an affinity ligand. An exemplary affinity resin includes affinity resins that bind to specific affinity tags attached to the target protein, such as an affinity tag incorporated into an ICAT-type reagent. The resolution and capacity of particular chromatographic media are known in the art and can be determined by those skilled in the art. The usefulness of a particular chromatographic separation for a particular application can similarly be assessed by those skilled in the art.

Those of skill in the art will be able to determine the appropriate chromatography conditions for a particular sample size or composition and will know how to obtain reproducible results for chromatographic separations under defined buffer, column dimension, and flow rate conditions. The fractionation methods can optionally include the use of an internal standard for assessing the reproducibility of a particular chromatographic application or other fractionation method. Appropriate internal standards will vary depending on the chromatographic medium or the fractionation method used. Those skilled in the art will be able to determine an internal standard applicable to a method of fractionation such as chromatography.

Electrophoresis, including gel electrophoresis or capillary electrophoresis, can also be used to resolve sample molecules. As disclosed herein, isoelectric focusing (IEF) is a particularly useful method to resolve sample polypeptides. Other types of electrophoresis can also be used, for example, sodium dodecyl sulfate polyacrylamide gel electrophoresis (SDS-PAGE) or acidurea gel electrophoresis. As discussed herein, sample molecules can be processed, for example, by protease cleavage into peptide fragments. Accordingly, when referring to sample molecules, the sample molecules can be intact as found in an original sample or can be processed, for example, into smaller molecules such as peptides from a polypeptide sample.

For generation of the ordered peptide array, a cocktail of the tagged, calibrated standard peptides is added to a peptide mixture generated by the digestion of the tagged protein sample. At this point, the sample mixture consists of all the peptides generated representing the digested protein sample and an external, calibrated standard for each one of the peptides that is be interrogated. The amount of tagged standard peptides added is estimated from the expected abundance of the protein in question. This abundance can be estimated from the codon bias tables or from previous experiments. The combined peptide mixture is subjected to multidimensional separation. The specific separation steps can include chromatography, for example, reverse phase, ion exchange, and affinity chromatography or other suitable chromatography steps, as disclosed herein. Affinity chromatography can be included to select tagged peptides in the case when a rare amino acid has been targeted with an ICAT™ reagent or other types of affinity chromatography, as disclosed herein; and gel electrophoresis, for example, IEF or other electrophoretic separations. The sample is separated into a plurality of fractions using one or more fractionation techniques, as disclosed herein.

Figure 2:
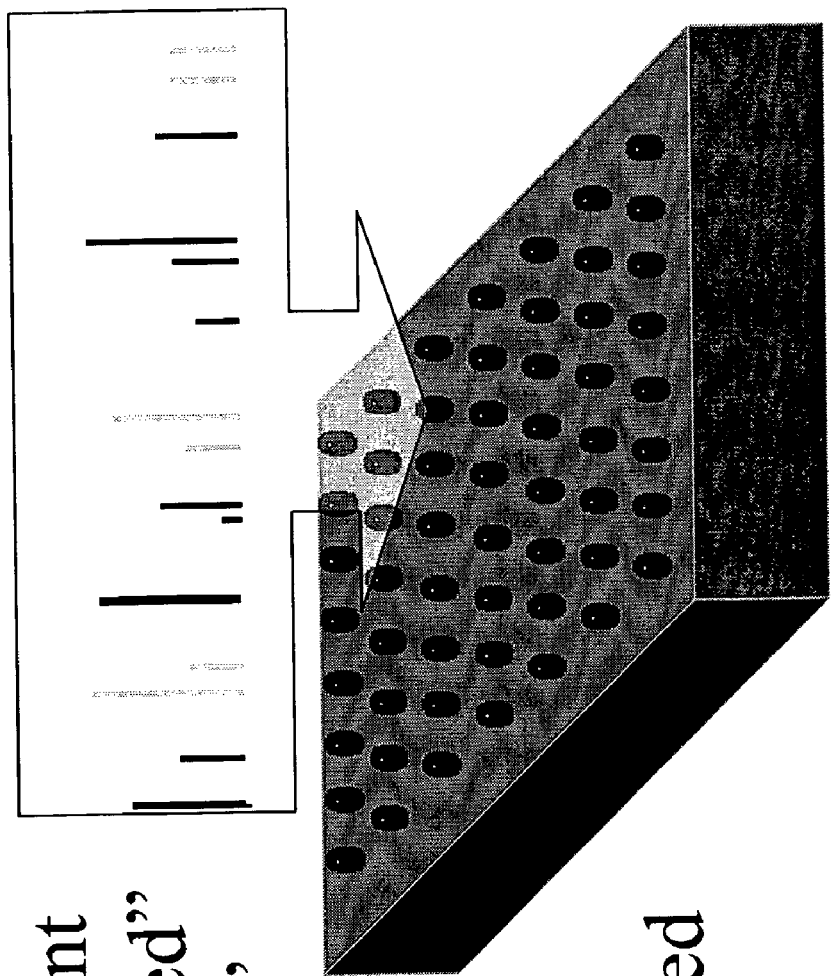
FIG. 2 shows a schematic diagram of an ordered peptide array and read out by matrix-assisted laser desorption/ionization (MALDI-MS). The sticks in the scheme indicate peptide signals that are detected by the MALDI-TOF mass spectrometer. It is apparent that some signals are detected as pairs of a mass difference that corresponds to the mass difference encoded in the isotope tag. These are indicated in yellow. The other signals appear as singlets and are not further considered for analysis because their mass does not correspond to the mass of an externally added standard peptide.

The fractions containing separated peptides can be spotted onto the sample plate of a MALDI mass spectrometer in the format of an ordered array (FIG. 2). The peptides are added with matrix mediating MALDI ionization using standard protocols. The precise address for each peptide has to be determined once or can be computed from the known properties of the target peptides. This can be done by sequencing of the peptides deposited in each sample spot using a MALDI-tandem mass spectrometer such as time-of-flight/time-of-flight or quadruople time-of-flight MS (TOF-TOF or qqTOF) or by the separation, deposition and MS analysis of defined pools of peptides. On the peptide array, each array element contains "expected" and "unexpected" peptides. The "expected" peptides are identified as paired signals of the differentially labeled standard peptides and sample peptides (FIG. 2).

A variety of mass spectrometry systems can be employed in the methods of the invention for identifying and/or quantifying a sample molecule such as a polypeptide. Mass analyzers with high mass accuracy, high sensitivity and high resolution include, but are not limited to, ion trap, triple quadrupole, and time-of-flight, quadrupole time-of-flight mass spectrometers and Fourier transform ion cyclotron mass analyzers (FT-ICR-MS). Mass spectrometers are typically equipped with matrix-assisted laser desorption (MALDI) or electrospray ionization (ESI) ion sources, although other methods of peptide ionization can also be used. In ion trap MS, analytes are ionized by electrospray ionization or MALDI and then put into an ion trap. Trapped ions can then be separately analyzed by MS upon selective release from the ion trap. Fragments can also be generated in the ion trap and analyzed. Sample molecules such as polypeptides labeled with an ICAT™ type reagent can be analyzed, for example, by single stage mass spectrometry with a MALDI-TOF or ESI-TOF system. Methods of mass spectrometry analysis are well known to those skilled in the art (see, for example, Yates, *J. Mass Spect.* 33:1-19 (1998); Kinter and Sherman, *Protein Sequencing and Identification Using Tandem Mass Spectrometry*, John Wiley & Sons, New York (2000); Aebersold and Goodlett, *Chem. Rev.* 101:269-295 (2001); Aebersold and Mann, *Nature* 422:198-207 (2003)).

While mass spectrometers using MALDI ionization are particularly useful in methods of the invention, it is understood that mass spectrometers equipped with ion sources of different types are also applicable in the methods of the invention. Specifically, mass spectrometers equipped with ESI ion sources are also suitable for methods of the invention. These include electrospray ionization time-of-flight (ESI-TOF) mass spectrometers and ESI aTOF, ion trap, triple quadrupole and FT-MS mass spectrometers.

Once the peptides are deposited as ordered arrays on the sample plate, they are analyzed by MS, for example, in a MALDI-TOF mass spectrometer. The instrument is programmed to sequentially generate mass spectra from each sample spot. Data acquisition from each spot is continued with further laser shots until mass spectra of a specific quality to detect the signals corresponding to peptide pairs have been generated. The mass spectra from each spot are written to a data-table and stored. Current mass spectrometers have a laser frequency of 20-30 Hz. It is expected that the laser frequency will increase to 200 Hz and later to minimally 1000 Hz. It is also estimated that for the interrogation of each sample spot, on the order of 100 laser shots are required. Therefore at 200 Hz laser frequency, the interrogation of a 96 spot sample plate will take about one minute, indicating that the methods can be applied for rapid and high throughput sample analysis. It is understood that, based on the needs of a particular sample analysis, one skilled in the art can use any desired configuration of fraction distribution on the array, including number of fractions on a particular array, and number of replicates, if desired. Furthermore, one skilled in the art can modify the configuration based on the type of MS analysis to be used, the number of fractions to be analyzed, the speed of data acquisition, and the desired accuracy of the data to be collected.

By distributing the resolved peptide fractions onto a mass spectrometry sample plate, an array is generated that can be used to assign the identification of a peptide to a known location. Once an array has been generated and defined and the locations of identified peptides stored in a database, a similar sample can be run under substantially similar conditions and the location on the array used to identify the peptide without the need for sequencing the resolved peptides. Thus, subsequent analysis of a similar sample can be performed more efficiently. Rather than performing the more detailed analysis required for sequencing, the MS analysis can be focused on quantitative analysis as well as identification of the peptides based on location on the array in combination with other characteristics determined by the MS analysis or provided by the position of the peptide on the array.

The distribution of resolved peptide fractions onto a MS sample plate serves to facilitate MS analysis, and further functions to convert the resolution of the fractions into coordinates on an array. As discussed above, once an array has been generated and the identity of particular peptides is correlated to a particular coordinate on the array, the identification of a subsequently analyzed sample peptide can be determined more efficiently based on its position on a similarly generated array. Thus, the distribution of fractions on an array and correlation of coordinates on the array with the identity of a peptide can be used to increase the efficiency of the analysis of similarly processed samples. Although the use of an array is particularly useful for such analysis, it is understood that the distribution on an array is not required to practice methods of the invention. For example, the samples can be analyzed using ESI-MS or ESI-MS/MS, without the need for distribution of fractions as an array on a MS sample plate. In such a case, information on the order of elution and the retention times of the resolved peptides is retained, for example, in a database.

Data analysis can be carried out using the following steps. First, in the mass spectrum of each sample spot, the ion signals are detected and de-isotoped. De-isotoping means collapsing all the signals of the same peptide that reflect the natural isotopic distribution (essentially the approximately 1% $^{13}C$ component of natural substances) and that are resolved in high resolution mass spectrometers such as the MALDI-MS system into a single peak. Second, pairs of peptide signals differing in mass by the number of stable isotope atoms introduced as part of the isotope tag in the sample versus standard peptides are detected.

Third, the signal for a specific ion pair is followed over 3 consecutive sample spots and summed up so as to minimize the impact of chromatographic isotope effects on quantification. Thus, if a particular peptide and its istopically labeled standard do not reside in a single fraction, its presence in neighboring fractions can be accounted for and added together for the quantitative analysis. Fourth, the detected peptide is identified by comparing its precise mass and the separation coordinates reflected in the array position with the entries in a database that contains the precise mass and the separation coordinates of all the standard peptides added to the sample mixture and processed under substantially similar conditions.

Fifth, from the combined signal intensities for a peptide pair, the ratio of abundance is calculated. Based on the known quantity of the external standard peptide, the absolute amount of the protein initially present in the sample is deduced. This operation is repeated for each sample spot and the data are compiled in a data-table for the experiment. Thus, the methods of the invention can be used to determine relative quantities of polypeptides present in the original sample as well as absolute quantities by comparison to the standard peptides.

Figure 3:
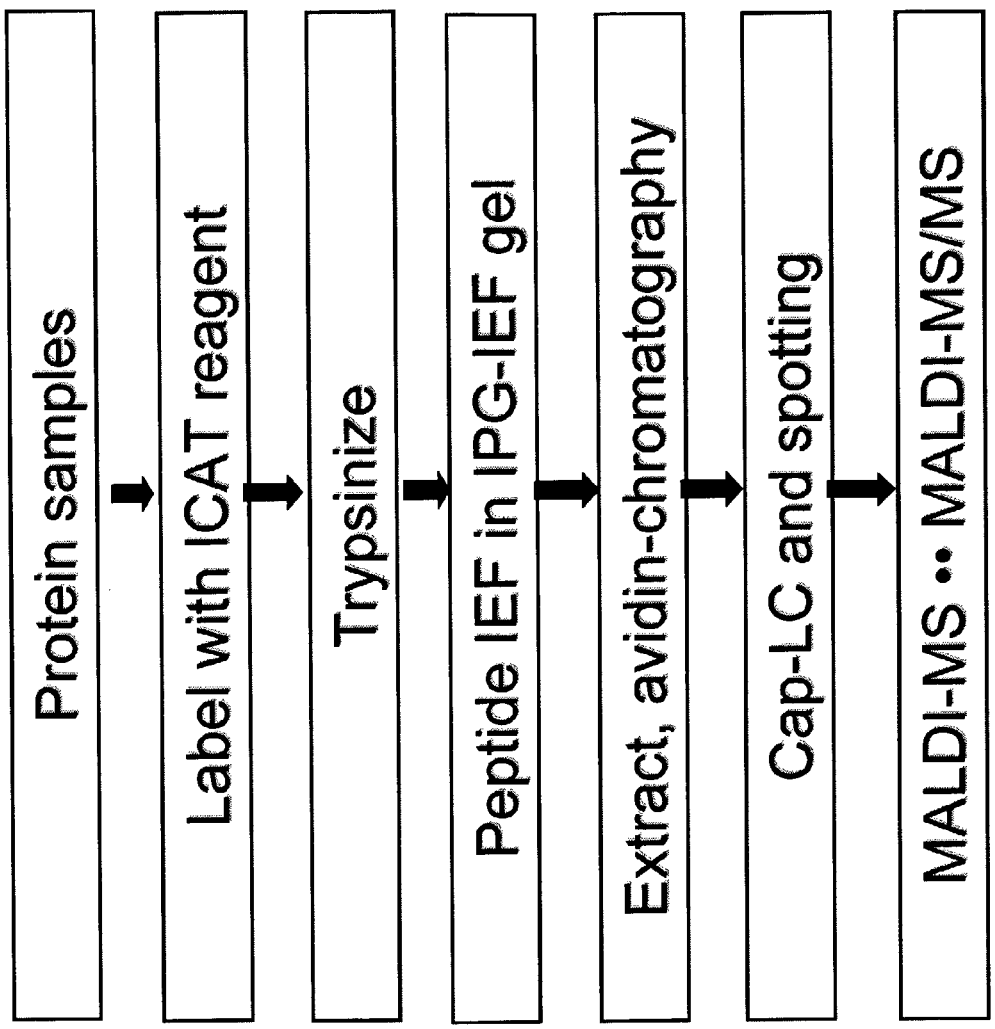
FIG. 3 shows a particular embodiment of the separation protocols, isotopic labeling, and MS analysis used for quantitative protein profiling.

An exemplary embodiment is shown in FIG. 3. In the illustrated embodiment, protein samples are labeled with an isotope tag, the ICAT™ reagent. The proteins are trypsinized and resolved by isolectric focusing (IEF) in immobilized pH gradient-IEF. Proteins are extracted from the gel and bound to avidin chromatography through the biotin affinity tag on the ICAT™ reagent. Affinity isolated peptides are resolved by capillary liquid chromatography, and resolved fractions are spotted on a MALDI plate. The array of peptides is analyzed by MALDI-MS and/or MALDI-MS/MS. Standard peptides are added to the sample peptides and resolved together for peptide identification and quantification.

Figure 4:
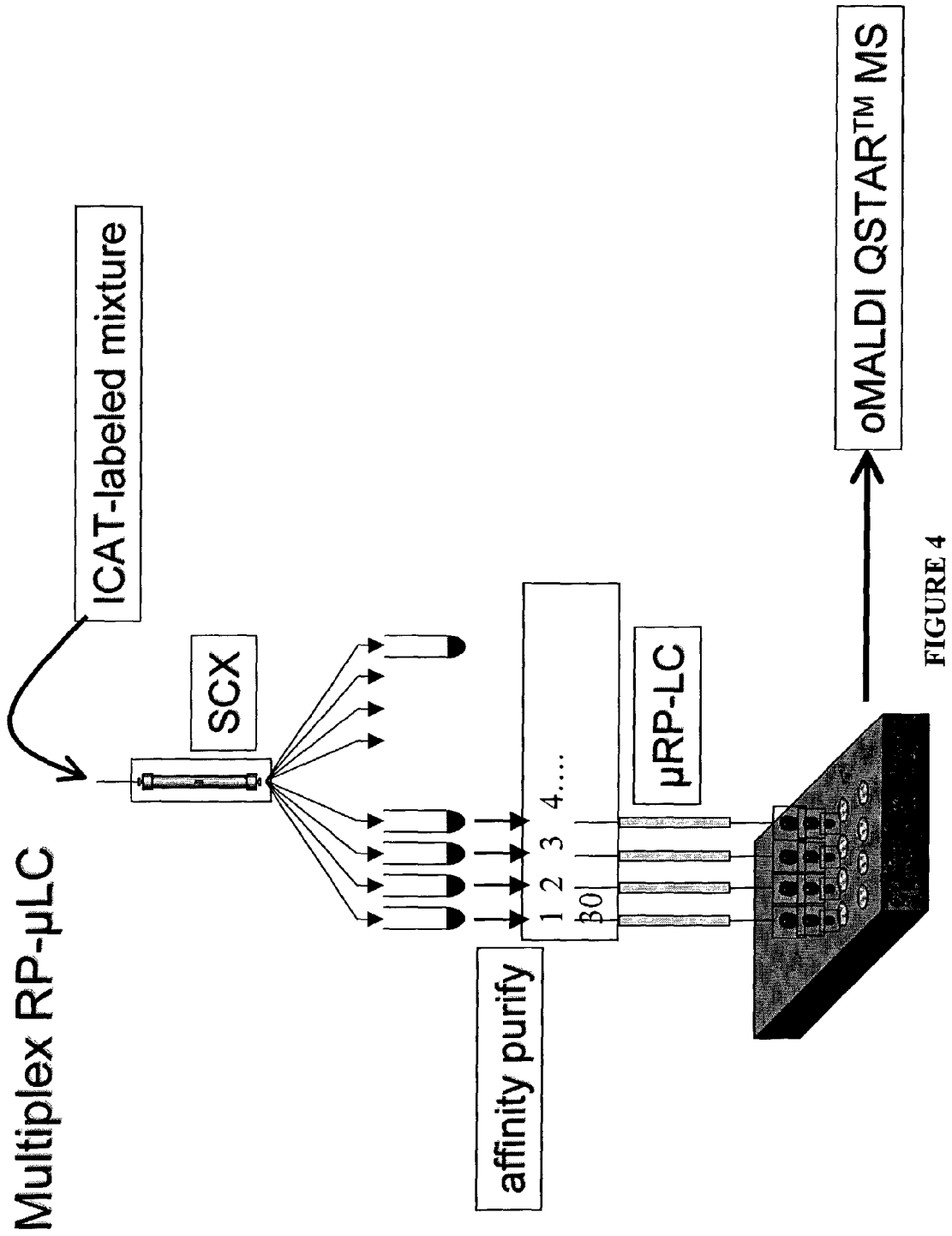
FIG. 4 shows a schematic representation of a method for generating ordered peptide arrays using capillary reverse-phase chromatography and spotting of the eluting peptides on a MALDI-MS sample plate.

Another embodiment of the invention is shown in FIG. 4, which illustrates multiplex reverse phase micro liquid chromatography. An ICAT™-labeled mixture of standard and sample peptides are resolved using strong cation exchange chromatography (SCX). The resolved fractions are affinity purified using the biotin tag of the ICAT™ reagent. The affinity purified fractions are further resolved using reverse phase micro liquid chromatography. The resolved fractions are spotted on a MALDI plate and analyzed by MS. This illustrates that multiple chromatography steps can be used to resolve peptides for MS analysis. The number of desired chromatography steps or other types of fractionation steps can be readily determined by one skilled in the art based on the needs of a particular application with respect to the need to resolve peptides sufficient for identification and/or quantification.

When comparing experimental data with that of a database, it is understood that the experimental data is obtained from substantially the same sample type as well as under substantially the same conditions. For example, if a serum sample is to be tested, the database or data-table for comparison of the sample should also be made with a serum sample. Alternatively, all the peptides from a species for which genomic sequence information is known can be calculated and stored in a single database, which can be annotated with known information indicating the tissue expression pattern, the subcellular location, or other known characteristics of the protein. Thus, the peptide standards that are used to generate the original array and from which information is stored in a data-table are added to a sample substantially similar to the test sample. Once a standard set of peptides has been resolved into identifiable fractions, the same identifiable fractions will result when the standard set of peptides is added to a test sample run under substantially similar conditions. One skilled in the art will know or can readily determine substantially similar conditions suitable for reproducible resolution of peptide fractions.

The methods of the invention can be used in a variety of applications. For example, the methods of the invention can be used for profiling blood serum. The ability to analyze readily accessible specimens such as blood serum is particularly useful for clinical applications. Thus, the methods are also applicable to basic biology and clinical analysis.

The methods of the invention can also be applied to the analysis of splice isoform mapping and profiling. Thus, differential splicing resulting in protein splice isoforms can be readily tested at the protein expression level. In the case of splice variants, peptide standards can be selected to assess a common portion as well as a portion of the sequence in which the splice isoforms differ, if desired. Thus, the invention provides a method for the quantitative profiling of splice and other protein isoforms. The invention also provides a method for the determination of the absolute quantities of splice and other protein isoforms.

The methods of the invention are also applicable to the mapping and profiling of post-translational modifications. Thus, the invention provides a method for the quantitative profiling of post-translational modifications.

For profiling of polypeptides having post-translational modifications, a modified peptide having a known post-translational modification is chemically synthesized and used in the methods of the invention, as described above. Methods for the synthesis of phosphorylated peptides are well known to those skilled in the art, and other types of modifications readily can be synthesized by those skilled in the art (Gerber et al., *Proc. Natl. Acad. Sci. USA* 100:6940-6945 (2003)). For mapping post-translational modifications, MS analysis can be used to identify modified peptides and the corresponding post-translational modifications.

Figure 5:
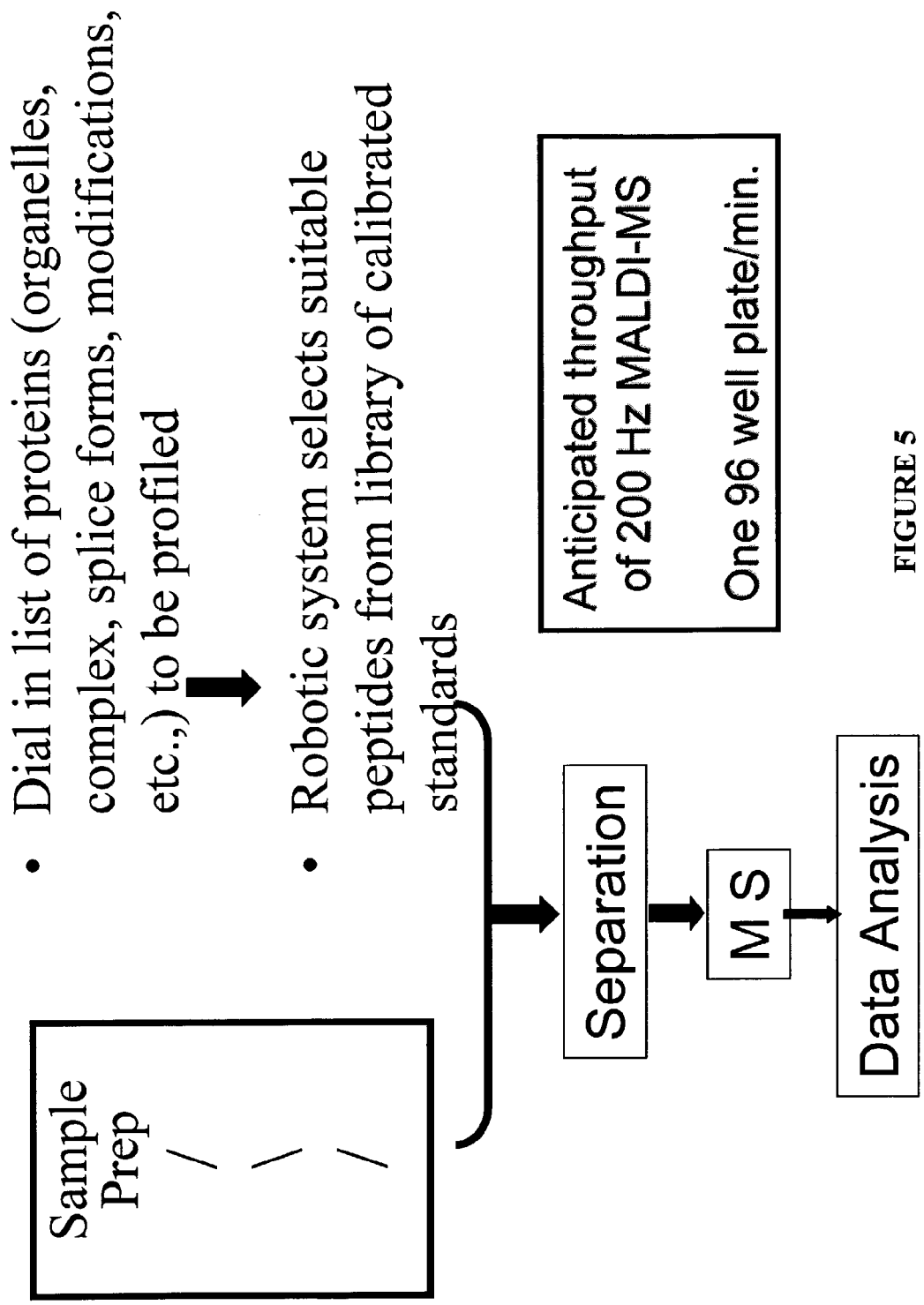
FIG. 5 shows a schematic representation of the method of protein profiling. A desired set of proteins to be profiled is selected, combined with sample peptides, and analyzed by MS.

The methods of the invention are advantageous for a variety of applications. For example, the methods allow the determination of absolute quantities of sample polypeptides by the inclusion of and comparison to known absolute amounts of standard peptides. Thus, the invention provides a method for quantitative proteome profiling, and can include the analysis of each of the standard peptides added to the test sample, if desired. It is understood, however, that the analysis and/or quantification of each of the added standard peptides need not be performed. The invention also provides a method for quantitative proteome profiling in which the absolute amount of sample polypeptide is determined. In the case of post-translational modification or isoform profiling, the stoichiometry of the different isoforms and/or modifications can be determined. FIG. 5 illustrates an exemplary embodiment, where a list of proteins in a desired organelle, complex, splice forms, or having post-translational modifications, is selected. In this illustration, an automated system is shown such that a robotic system selects suitable peptides from a library of calibrated standards for analysis of a particular sample. Sample peptides are labeled with a corresponding differential isotope tag and digested according to the designed standard peptides. Sample and standard peptides are combined, resolved using one or more fractionation methods, and analyzed by MS. The results of the MS analysis are used to identify and/or quantify sample peptides corresponding to the added standard peptides.

The methods of the invention can be applied to look specifically at subproteomes, if desired. Subproteomes refer to fractions of the proteome of a cell or tissue that can be reproducibly isolated. Subproteomes include the protein contents of organelles, for example, mitochondria, chloroplasts, peroxisomes, lysosomes, and the like; subcellular fractions such as nuclear fraction, microsomal fraction, plasma membrane fraction, cytoplasmic fraction; specific protein complexes such as splicosomes or ribosomes; specific classes of enzymes, for example, kinases, phosphatases, serine hydrolases, and the like; or proteins that are modified by a common post-translational modification, for example, phosphorylated or glycosylated proteins, or other post-translational modifications. FIG. 5 illustrates an exemplary embodiment, where a list of proteins in a desired organelle, complex, splice forms, modifications, is selected. In this illustration, an automated system is shown such that a robotic system selects suitable peptides from a library of calibrated standards for analysis of a particular sample. The peptides are resolved (separated), subjected to MS analysis and analyzed. The illustrated automated system is capable of analyzing about one 96-well plate per minute.

If desired, the sample can be processed so that a subset of polypeptides in the original sample is analyzed (see Example I). For example, it is possible to isolate glycopolypeptides by specifically absorbing oxidized glycopolypeptides to a hydrazide resin. If desired, N-glycosylated peptides can be selectively analyzed by using an N-glycosidase to release glycopeptides bound to the hydrazide resin. Methods of isolating phosphoproteins are also well known to those skilled in the art and can be applied to isolate a subset of polypeptides that are phosphorylated (Zhou et al., 19:375-378 (2001)).

Thus, the invention also provides methods for quantitative profiling of protein modifications, which can be determined in absolute amounts when known absolute amounts of standard peptides are added to the sample peptides. The invention thus provides a method of identifying and quantifying phosphorylated polypeptides by isolating phosphorylated polypeptides using well known methods and applying the methods of the invention to profile the phosphorylated polypeptides.

The invention also provides a method for quantifying polypeptides in a sample. The method can include the steps of labeling peptides in a polypeptide sample with an isotope tag; adding a known absolute amount of a plurality of peptide standards to the polypeptide sample, wherein the peptide standards are labeled with an isotopically distinct version of the isotope tag; resolving the labeled sample and standard peptides into a plurality of fractions; analyzing the resolved fractions using mass spectrometry; identifying an isotope-tagged sample peptide in an analyzed fraction; and determining the amount of the identified isotope-tagged sample peptide in the analyzed fraction by comparison to the amount of isotope tagged standard peptide in the same fraction.

The invention additionally provides a method for identifying and/or quantifying splice isoforms of polypeptides in a sample. The method can include the steps of labeling peptides in a polypeptide sample with an isotope tag; adding a plurality of peptide standards to the polypeptide sample, wherein the peptide standards are labeled with an isotopically distinct version of the isotope tag and wherein the plurality of peptide standards comprises at least one peptide corresponding to a common amino acid sequence of a splice isoform of a polypeptide and at least one peptide corresponding to an amino acid sequence that differs between two splice isoforms of the polypeptide; resolving the labeled sample and standard peptides into a plurality of fractions; analyzing the resolved fractions using mass spectrometry; identifying an isotope-tagged sample peptide in an analyzed fraction; and determining the amount of the identified isotope-tagged sample peptide in the analyzed fraction by comparison to the amount of isotope tagged standard peptide in the same fraction.

As discussed above, the methods of the invention can be used to generate an array of known peptides for a particular type of sample. The information on the location of peptide standards on the array can be stored in a database and referenced when similar test samples are analyzed. Thus, the information obtained and stored based on an original set of peptide standards resolved under a given set of conditions can be repeatedly accessed for comparison of a similar test sample. Furthermore, different arrays can be generated for different types of samples and the information on peptide locations saved for future analysis of similar types of test samples. Thus, the methods of the invention can be used to develop "arrays" that are specific for a number of applications. Arrays can be generated to analyze various types of samples, for example, blood serum, lymphocytes, organelle or subcellular fractions such as nuclear extracts, extracts of mitochondria, chloroplasts, peroxisomes, lysosomes, membrane, cytoplasmic fractions, and the like, as disclosed herein.

The methods of the invention can be applied to a number of species so long as a sufficient amount of sequence information is available. The level of sequence information sufficient to determine one or a few signature peptides for a parent polypeptide can readily be determined by one skilled in the art based on the needs of the particular application. The methods are particularly useful for organisms where partial, nearly complete or essentially complete genomic sequence is available. Thus, as the genomes of additional species are determined, the methods of the invention can be readily adapted for proteomics analysis of these species.

The methods of the invention are additionally advantageous because they obviate the need for antibodies, aptamers or other reagents that are specific for a particular protein for the analysis of polypeptide expression profiles. For some previously described methods of proteome analysis, a specific antibody, aptamer or other type of specific reagent must be generated for each polypeptide to be analyzed. However, in the present invention, all that is needed is a synthetic peptide, which can be generated in a few hours, and many peptides can be generated in parallel. Furthermore, the probes for sample analysis are easily standardized, quality controlled and distributed since the peptide standards can be accurately determined in absolute quantities and their chemical composition, degree of purity and amino acid sequence are easily verified using well known methods. Because a set of easily synthesized peptide standards are used, the collection of peptide standards used to probe the test samples is easily updated if new genes or isoforms are discovered.

The methods of the invention allow the determination of relative and absolute quantities of polypeptides in a test sample. Polypeptides are expressed at a wide range of amounts, with some very abundant polypeptides present in a sample along with low abundance polypeptides. The wide range of expression between individual polypeptides in a sample can cause difficulties in their analysis because the low abundance proteins can be obscured and not easily detectable among the signals of the highly expressed proteins. The methods of the invention, however, allow an estimation of the approximate abundance of each peptide, reducing problems associated with the abundance range of polypeptides expressed in a sample.

The methods of the invention also provide sensitivity, speed, and high throughput for the analysis of complex polypeptide samples. By generating an ordered array, the location of specific peptides on the array can be determined once, with subsequent analysis of test samples not requiring the need to sequence peptides in order to identify them. In subsequent analysis of test samples, only the peptide mass has to be measured rather than determination of the sequence of the peptide, resulting in the method being very sensitive, in the subfemtomole range.

Furthermore, even if the peptides are sequenced in every experiment, that is, if the peptide sequence is not deduced by the position of the peptide on the array but by direct sequencing, for example, using a MALDI tandem mass spectrometer, the methods of the invention are still advantageous in terms of sample throughput. The peptides that are to be sequenced are characterized by their presence in the array as isotopic pairs of a precisely known mass difference. All the other peptides, that is, the peptides from proteins that are not being interrogated and other peptides from proteins for which one or a few peptides have been selected for analysis will appear as a singlet and can therefore be excluded from further analysis.

The invention additionally provides a set of polypeptides that uniquely identify a set of parent polypeptides. The invention also provides reagents and kits for identifying and quantifying polypeptides in a sample. The kit can contain, for example, a collection of peptide standards having an isotope tag. For example, the kit can contain a set of calibrated synthetic standard peptides of known relative or absolute amounts. The kit can also include a set of one or more isotope tags differentially labeled from that of the standard peptides for coupling to sample polypeptides, which are particularly useful for quantitative analysis using mass spectrometry. The kit can also contain one or more reagents for purification of sample peptides, for example, chromatography columns, electrophoresis gels, and the like, as well as a protease(s) or other cleavage reagent corresponding to the cleavage method used to derive the peptide standards. The contents of the kit of the invention, for example, any standard peptides or labeling reagents, are contained in suitable packaging material, and, if desired, a sterile, contaminant-free environment. In addition, the packaging material can contain instructions indicating how the materials within the kit can be employed to label sample molecules. The instructions for use typically include a tangible expression describing the reagent concentration or at least one assay method parameter, such as the relative amounts of reagent and sample to be admixed and how to adjust the amounts if needed for quantification, maintenance time periods for reagent/sample admixtures, temperature, buffer conditions, and the like. The kits also can include MALDI MS sample plates for the formation of the peptide arrays, matrix molecules for MALDI MS and suitable solvents for sample preparation.

The methods of the invention can be facilitated by the use of combinations of hardware and software suitable for analysis of methods of the invention. Computer memory and data storage capacity as well as appropriate algorithms can be used to facilitate carrying out any or all of the following steps of the invention or any other steps of the invention: generation of a peptide database in which the sequence and properties of the peptides added as external standards are recorded; the step of detecting the peptide pairs (sample and standard) and of calculating the relative abundance of the peptide pairs; the step of identifying the peptide by correlating the separation coordinates and the precise mass with the recorded database of sequence and other properties of the peptides or by sequencing of the peptides using, for example, a MALDI-tandem mass spectrometer; the step of converting the individual peptide datapoints into a quantitative protein profile and of displaying that profile; and the step of comparing multiple quantitative profiles with each other for the detection of differences in the protein expression profiles of different samples.

Figure 6:
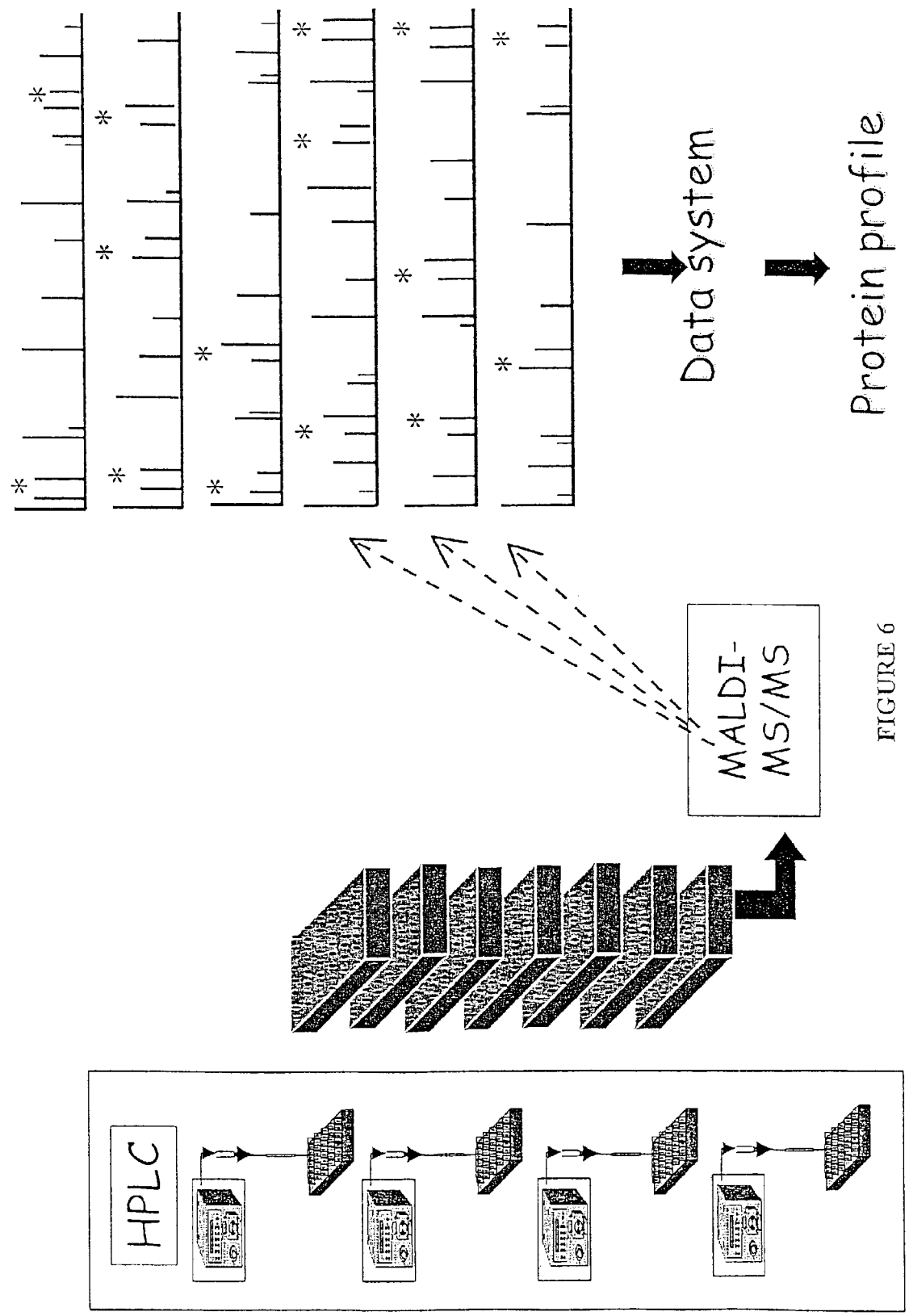
FIG. 6 shows a schematic representation of the mass spectrometry analysis for protein profiling. Proteins are resolved into fractions, which are deposited on a MS plate, and analyzed by MALDI-MS/MS to generate a protein profile. Differential isotopically labeled pairs of standard and sample peptides are indicated by "*".

An exemplary automated system is illustrated in FIG. 6. FIG. 6 shows the generation of an ordered peptide array using HPLC separation of proteins. The ordered array(s) is analyzed by MS. Pairs of differential isotopically labeled sample and standard peptides are shown (*). The addition of a known amount of standard peptides allows both identification and quantification of the purified peptides (FIG. 6). Other peptides, which are not paired with standard peptides, can be ignored, allowing resources to be focused on the peptides of interest.

Figure 7:
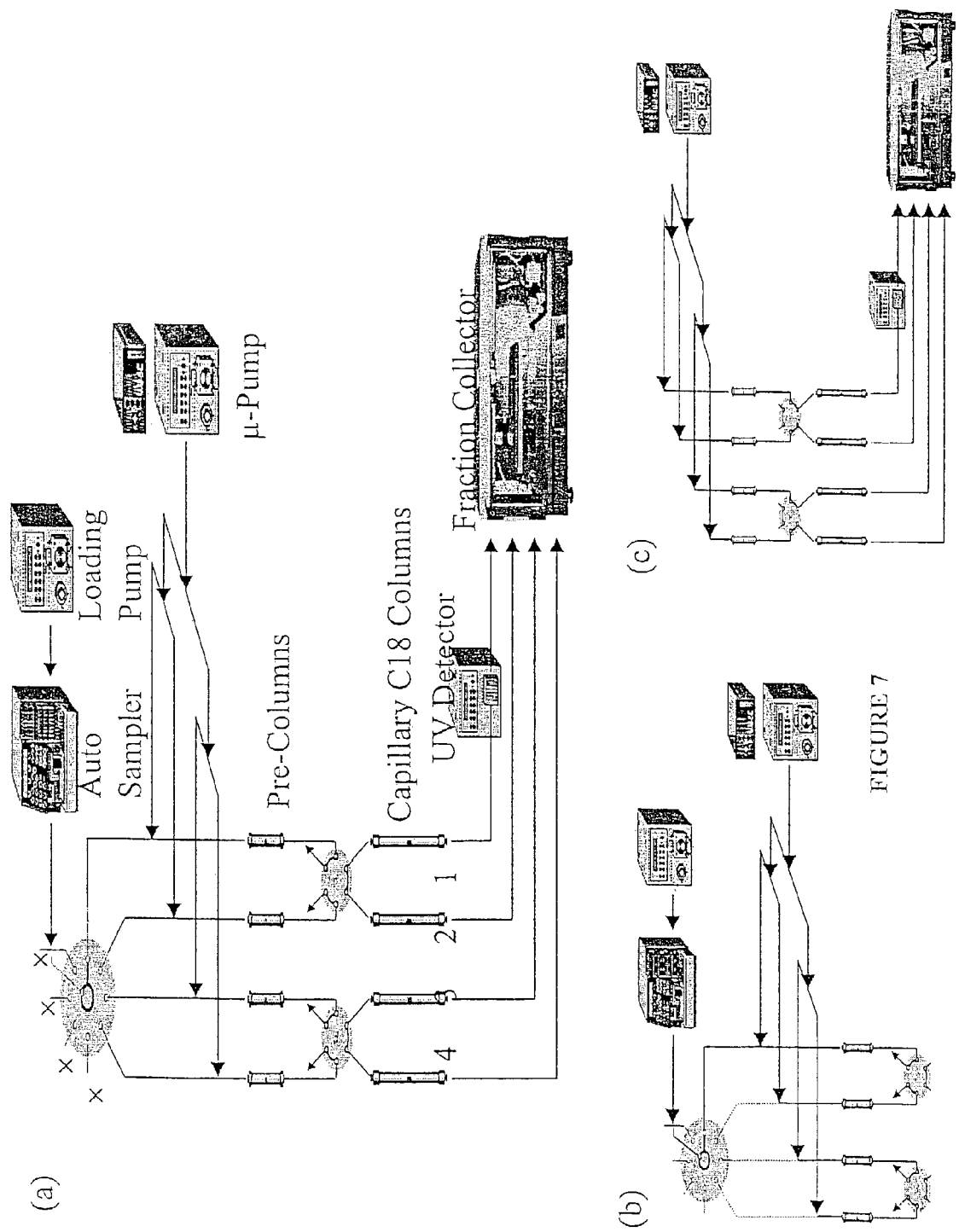
FIG. 7 shows a diagram of a format for protein profiling.

FIG. 7 shows an embodiment of an automated format for protein profiling. FIG. 7A shows a schematic representation of the fourplexed reverse phase micro fluid chromatography (RP-µLC) system. The system components can be segmented into four modules: sample loading, solvent delivery, separation, and fractionation. FIG. 7B shows the flow-path and valve configurations at the injection stage of the fourplexed RP-µLC system. FIG. 7C shows the flow-path and valve configurations at the separation stage of the fourplexed RP-µLC system. It is understood that this and a number of other arrangements of components is suitable for use in methods of the invention.

The invention provides methods of identifying and/or quantifying polypeptides in a sample. It is understood that methods of the invention can be carried out in any suitable order so long as the desired identification and quantification of sample peptides is achieved. It is further understood that the methods disclosed herein can be directed to identification and/or quantification, as desired. The invention also provides reports and methods of reporting the results of methods of the invention for identifying and/or quantifying polypeptides in a sample.

It is understood that modifications which do not substantially affect the activity of the various embodiments of this invention are also provided within the definition of the invention provided herein. Accordingly, the following examples are intended to illustrate but not limit the present invention.

EXAMPLE I

Quantitative Protein Profiling in Body Fluids

This example describes quantitative protein profiling in a serum sample.

Human blood serum is subjected to a procedure that selectively isolates a representative population of peptides. Human blood serum is isolated using well known methods, and polypeptides in the serum are purified by well known methods (see, for example, Scopes, supra, 1993). The serum proteins are denatured in 6M urea and the disulfide bonds are reduced with DTT, tributylphosphine, β-mercaptoethanol, tris-carboxyethylphosphine (TCEP), or other common reducing reagents. Proteins are then labeled with an ICAT reagent (Gygi et al., supra, 1999) or similar isotope tagging reagents following standard protocols. The polypeptides are then digested with a protease such as trypsin to generate peptide fragments.

The peptide fragments are tagged with a suitable isotope tagging reagent. For example, the peptide fragments can be tagged with an ICAT™-type reagent. The reactive group can be reactive for a subset of peptides, such as a sulfhydryl reactive group which can couple to cysteine residues. If a large number of the peptides are to be analyzed, for example, in cases in which more complete sequence coverage is to be achieved or if the selected peptide does not contain a cysteine residue, a more general reactive group such as an amino or carboxyl reactive group can be used since the majority of cleaved peptides would contain a free carboxyl and/or amino group. A collection of peptide standards are synthesized and tagged with the same tag used to tag the proteins except that the peptide standards are differentially isotope tagged. For example, the peptides can be labeled with an amino group specific tagging reagent if glycopeptides are bound to a hydrazide solid support (see below). The labeled peptides are eluted, for example, using an N-glycanase, separated and sequenced.

The set of isotope-tagged peptide standards is added to the isotope-tagged sample peptides. The peptides are separated using one or more separation techniques and deposited on the sample plate in an array format. An exemplary separation protocol includes peptide separation by IEF followed by capillary reverse phase high performance liquid chromatography (RP-HPLC). Alternatively, the separation method can be multidimensional chromatography, for example, ion exchange, reverse phase, and the like. The separation method can also be extended single dimensional chromatography, where chromatographic separation is performed to optimize peptide separation with a single chromatography method, for example, with shallower slope of eluant.

A selected subset of the detected peptides are chemically synthesized and tagged with the light form of the reagent. Alternatively, the peptide standards can be tagged with the heavy form, so long as distinct isotopic forms are used between the standard and sample peptides. The subset is selected based on known sequences in the genome and/or previous empirical determination of the identity of polypeptides in the aserum sample. In some applications, the peptides are selected to achieve as complete coverage of the serum proteome as possible with easily separable, soluble and idiotypic peptides.

Typically, the peptide standard is added at the beginning of the process, generally after tryptic cleavage and before sample separation. In an initial experiment, before the selection of peptides for synthesis is made, the digests of a serum sample prepared the same way are sequenced by tandem mass spectrometry.

Subsequent to the determination of the separation coordinates of the peptides selected for synthesis as standard peptides, similar serum protein samples to be profiled are processed in the same manner as the one used for the generation of the original peptide list, except that the selected mixture of tagged standard peptides is added to the tagged serum sample after trypsinization. The combined mixture of sample and standard peptides labeled with differential isotopes are separated and spotted onto a MALDI-MS sample plate. Each sample spot is interrogated by mass spectrometry.

Alternatively, serum glycoproteins can be analyzed. For analysis of glycopolypeptides from serum samples, 2.5 ml of human serum (200 mg total protein) such as human serum were changed to buffer containing 100 mM NaAc, 150 mM NaCl, pH 5.5 using a desalting column (Bio-Rad; Hercules Calif.). Sodium periodate solution at 15 mM was added to the samples. The cap was secured and the tube is covered with foil. The sample was rotated endover-end for 1 hour at room temperature. The sodium periodate was removed from the samples using a desalting column. A 50 µl aliquot of the sample was taken before lo coupling the sample. To the sample was added 8 ml of coupling buffer equilibrated hydrazide resin (Bio-Rad). The sample and resin were capped securely and rotated end-over-end for 10-24 hours at room temperature. After the coupling reaction was complete, the resin was spun down at 1000×g for 10 min, and non-glycoproteins in the supernatant were removed. A 50 µl aliquot of the post conjugation sample was taken.

For analysis of glycosylated peptides, non-specific proteins bound to the resin were washed away extensively by washing the resin 3 times with an equal volume of 8M urea/0.4M $NH_4HCO_3$. The proteins on the resin were denatured in 8M urea/0.4M $NH_4HCO_3$ at 55° C. for 30 min followed by 3 washes with the urea solution. After the last wash and removal of the urea buffer, the resin was diluted 4 times with water. Trypsin was added at a concentration of 1 µg of trypsin/100 µg of protein and digested at 37° C. overnight. The trypsin released peptides were removed by washing the resin with an equal volume of 1.5 M NaCl for 3 times, 80% MeCN/0.1% TFA for 3 times, 100% methanol for 3 times, and 0.1 M $NH_4HCO_3$ for 6 times. The released non-glycosylated peptides can be saved and optionally labeled with an isotope tag for further analysis. The bound glycopolypeptides can be labeled with an isotope tag, essentially as described above, using an amino or carboxyl reactive group on the isotope tagging reagent. N-linked glycopeptides are released from the resin by digestion with N-glycosidase at 37° C. overnight. The resin is spun and the supernatant saved. The resin is washed twice with 80% MeCN/0.1% TFA and combined with the supernatant. The resin is saved for O-linked glycopeptide release later.

The peptides are dried in tubes, and one tube is resuspended in 50 µl of 0.4% acetic acid. A 3 µl aliquot of the sample is loaded on a capillary column for µLC-MS/MS analysis. CID spectra are searched against a database corresponding to the species of the serum sample, for example, a human database, using SEQUEST (Eng, J. et al., J. Am. Soc. Mass. Spectrom. 5:976-989, (1994)) to identify the glycopeptides and glycoproteins. The pairs of peptides differing by the isotope tag are compared for quantification of the corresponding sample peptides, as disclosed herein.

EXAMPLE II

Quantitative Profiling of Proteins Contained in Human Mitochondria

This example describes profiling of proteins in human mitochondria.

Mitochondria, as an exemplary organelle, are isolated using standard methods. Human cultured cells grown in a suitable tissue culture medium are harvested by centrifugation, washed free of serum by triplicate washing in buffered saline solution and homogenized. To isolate the mitochondria, the lysate is subjected to a series of differential centrifugation steps. A fraction highly enriched for mitochondria is isolated from a 20,000×g pellet by isopycnic centrifugation on a discontinuous Nycodenz gradient. A protein extract from the separated mitochondrial fraction is prepared using standard methods (Scopes, supra, 1993). The proteins are analyzed essentially as outlined in Example I, except that the tagged standard peptides are selected to represent all or the majority of known human mitochondrial proteins. The peptide samples to be synthesized are determined by sequence analysis of a similarly prepared mitochondrial peptide sample.

EXAMPLE III

Quantitative Profiling of Proteins Contained in Whole Cell Lysates

This examples describes protein profiling of whole cell lysates.

Human cultured cells are grown and harvested essentially as described in Example II, except that cultured cells are harvested by centrifugation and washing, and then the cells are lysed. Whole cell lysates are prepared using standard protocols (Scopes, supra, 1993). Lysis conditions to isolate most of the proteins is carried out by lysis of the cells in 1% SDS.

Protein profiling of the whole cell lysates is carried out essentially as described in Examples I and II except that the tagged standards are selected to represent all or the majority of known human proteins or proteins known to be present in the particular tissue type corresponding to the cultured cells used for analysis.

EXAMPLE IV

Quantitative Profiling of Protein Splice Variants

This example describes profiling of protein splice variants.

A cell or tissue sample is prepared essentially as described in Examples II and III using well known methods (Scopes, supra, 1993). The peptides selected as external standards are chosen based on known or empirically determined splice variants. The peptide standards are selected such that, for each alternatively spliced protein, minimally one peptide is used that is common to all splice variants and minimally one peptide is used that is unique for each splice variant tested. Protein profiling is carried out essentially as described in Examples I-III.

EXAMPLE IV

Reproducible Fractionation of Peptides

This example shows that parallel purification is reproducible.

Figure 8:
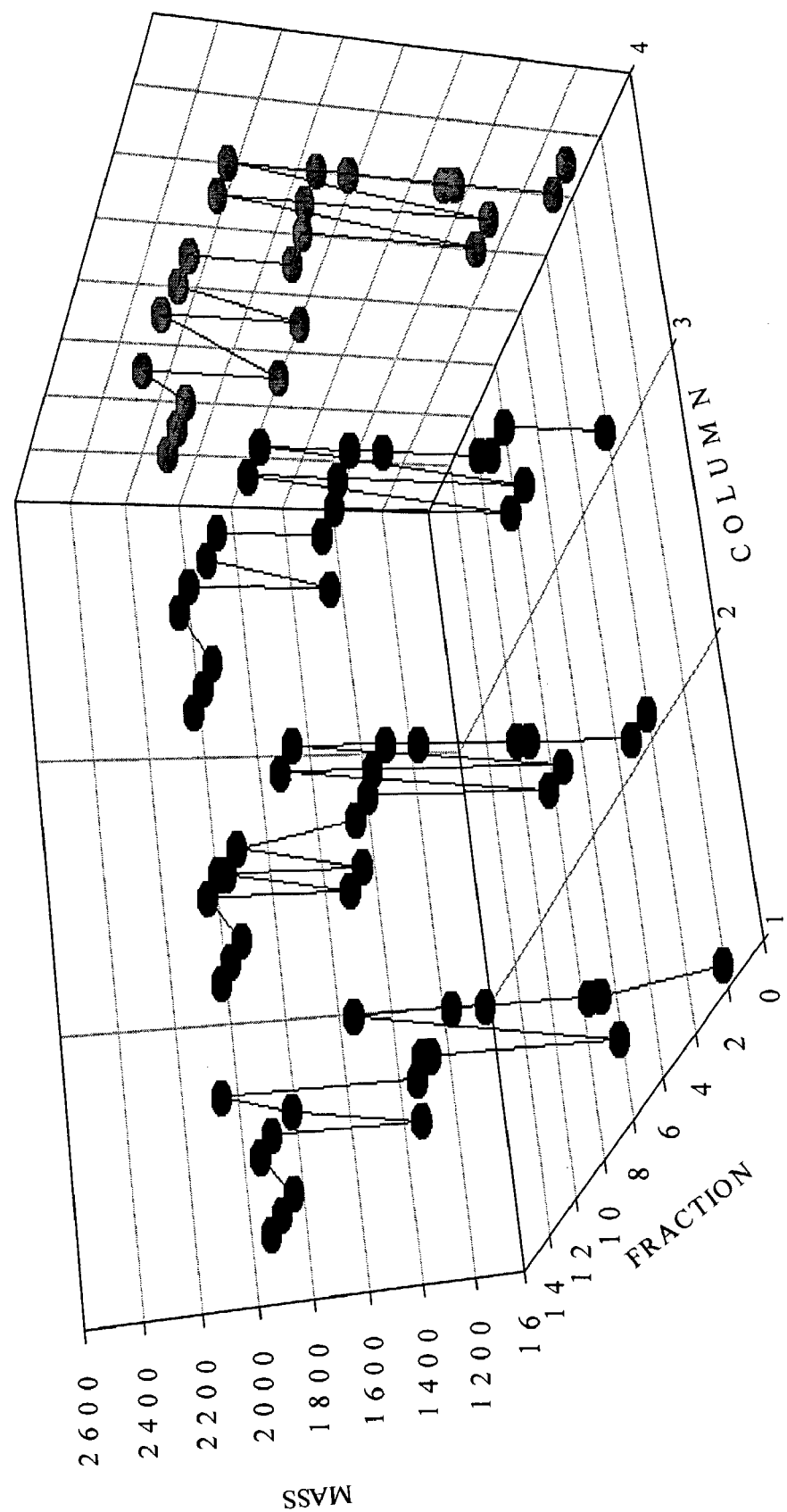
FIG. 8 shows elution profiles of ICAT™ reagent labeled bovine serum albumin (BSA) tryptic peptides eluted from the four parallel columns. Peptides were identified using a MALDI QqTOF mass spectrometer.

Peptides were analyzed essentially as described in Example I and disclosed herein. Briefly, bovine serum albumin (BSA) was labeled with ICAT™ reagent essentially as described in Example I. Tryptic digests were analyzed on parallel columns. FIG. 8 shows the elution profiles of ICAT™ reagent labeled BSA tryptic peptides eluted from the four parallel columns. Peptides were identified using a MALDI QqTOF mass spectrometer.

EXAMPLE V

Quantitative Peptide Profiling via MALDI-MS and MALDI-MS/MS

This example shows quantitative peptide profiling via MALDI-MS and MALDI-MS/MS.

Figure 9:
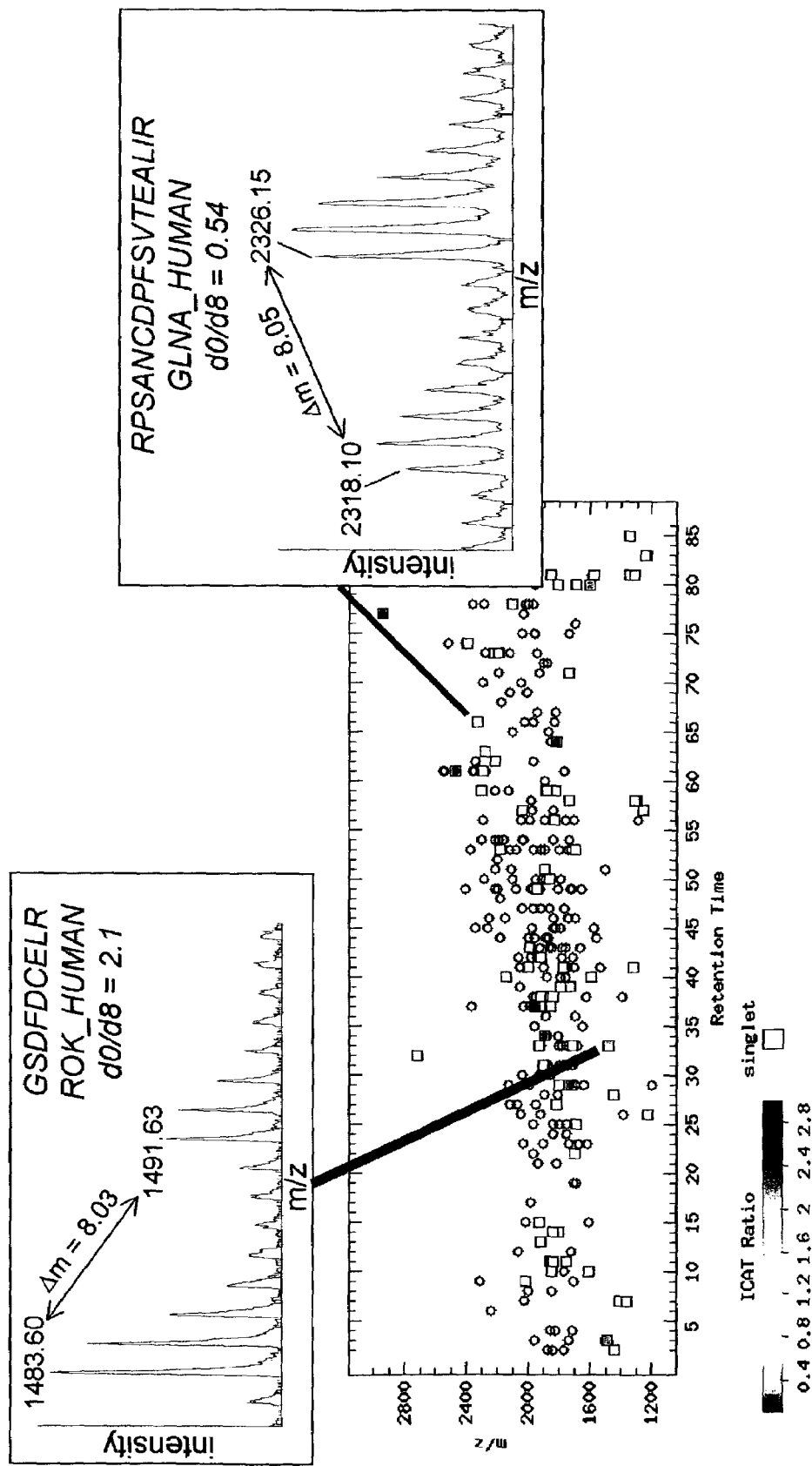
FIG. 9 shows quantitative peptide profiling via MALDI-MS and MALDI-MS/MS. Protonated peptide masses (M+H) of automatically determined, putative ICAT™ reagent labeled peptides derived from human prostate cells are plotted against chromatographic retention time. Circles indicate constitutively represented peptides, while colored squares indicate peptides showing significant abundance changes. Representative results from two identified, differentially expressed peptides (SEQ ID NOS:1 and 2, left and right) are shown.

Samples derived from human prostate cells were labeled with the ICAT™ reagent and analyzed essentially as described in Example I and disclosed herein. FIG. 9 shows quantitative peptide profiling via MALDI-MS and MALDI-MS/MS. Protonated peptide masses (M+H) of automatically determined, putative ICAT™ reagent labeled peptides derived from human prostate cells are plotted against chromatographic retention time. Circles indicate constitutively represented peptides, while colored squares indicate peptides showing significant abundance changes. Representative results from two identified, differentially expressed peptides are shown.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method of identifying and quantifying polypeptides in a sample, comprising the steps of:
   (a) cleaving a polypeptide sample to generate sample peptides;
   (b) labeling the sample peptides with a first isotope tag to provide a sample of a first isotopically-labeled peptide;
   (c) chemically synthesizing a plurality of peptide standards of known sequences, wherein the chemically synthesized peptide standards of known sequences comprise sequences of peptides generated by the same cleaving as in step (a);
   (d) labeling the chemically synthesized peptide standards with a second isotope tag, wherein the second isotope tag labels the chemically synthesized peptide standards with an isotopically distinct version of the first isotope tag, thereby generating a plurality of isotopically-labeled chemically synthesized peptide standards;
   (e) adding the plurality of the isotopically-labeled chemically synthesized peptide standards of known sequences to the isotopically-labeled sample peptides, thereby generating a mixture of isotopically-labeled sample peptides and isotopically-labeled chemically synthesized peptide standards;
   (f) resolving the mixture of labeled sample peptides and labeled chemically synthesized peptide standards into a plurality of resolved fractions;
   (g) analyzing the resolved fractions by mass spectrometry;
   (h) identifying an isotopically-labeled sample peptide in an analyzed fraction from step (g); and
   (i) determining the amount of the identified isotopically-labeled sample peptide in the analyzed fraction by comparing the amount of the identified isotopically-labeled sample peptide to the amount of the isotopically-labeled chemically synthesized peptide standard in the analyzed fraction.

2. The method of claim 1, wherein the analyzing by mass spectrometry comprises depositing the plurality of fractions onto a mass spectrometry sample plate.

3. The method of claim 1, wherein a known absolute amount of each of the known synthetic peptide standards is added to the peptide sample.

4. The method of claim 1, wherein the cleaving of the polypeptide sample comprises cleaving with a protease.

5. The method of claim 4, wherein the protease is trypsin.

6. The method of claim 1, wherein the polypeptide sample is obtained from a body fluid selected from the group consisting of blood, plasma, serum, cerebrospinal fluid, urine, saliva, seminal plasma, and pancreatic juice.

7. A method of identifying and quantifying polypeptides in a sample, comprising the steps of:
   (a) cleaving a polypeptide sample to generate sample peptides;
   (b) labeling the sample peptides with a first isotope tag to provide a sample of a first isotopically-labeled peptide;
   (c) synthesizing a plurality of peptide standards of known sequences by recombinantly expressing the peptide standards, wherein the peptide standards of known sequences comprise sequences of peptides generated by the same cleaving as in step (a);
   (d) labeling the peptide standards with a second isotope tag, wherein the second isotope tag labels the peptide standards with an isotopically distinct version of the first isotope tag, thereby generating a plurality of isotopically-labeled recombinantly expressed peptide standards;
   (e) adding a plurality of the isotopically-labeled peptide standards of known sequences to the isotopically-labeled sample peptides, thereby generating a mixture of isotopically-labeled sample peptides and isotopically-labeled peptide standards;
   (f) resolving the mixture of labeled sample peptides and labeled peptide standards into a plurality of resolved fractions;
   (g) analyzing the resolved fractions by mass spectrometry;
   (h) identifying an isotopically-labeled sample peptide in an analyzed fraction from step (g); and
   (i) determining the amount of the identified isotopically-labeled sample peptide in the analyzed fraction by comparing the amount of the identified isotopically-labeled sample peptide to the amount of the isotopically-labeled peptide standard in the analyzed fraction.

8. The method of claim 7, wherein each of the synthetic peptide standards is recombinantly expressed as a single peptide product.

9. The method of claim 7, wherein each of the synthetic peptide standards is recombinantly expressed as a concatenated peptide product.

10. The method of claim 7, wherein the analyzing by mass spectrometry comprises depositing the plurality of fractions onto a mass spectrometry sample plate.

11. The method of claim 7, wherein a known absolute amount of each of the known synthetic peptide standards is added to the peptide sample.

12. The method of claim 7, wherein the cleaving of the polypeptide sample comprises cleaving with a protease.

13. The method of claim 12, wherein the protease is trypsin.

14. The method of claim 7, wherein the polypeptide sample is obtained from a body fluid selected from the group consisting of blood, plasma, serum, cerebrospinal fluid, urine, saliva, seminal plasma, and pancreatic juice.

15. A method of identifying and quantifying polypeptides in a sample, comprising the steps of:
   (a) cleaving a polypeptide sample to generate sample peptides;
   (b) labeling the sample peptides with a first isotope tag to provide a sample of a first isotopically-labeled peptide;
   (c) chemically synthesizing a plurality of peptide standards of known sequences, wherein the chemically synthesized peptide standards of known sequences comprise sequences of peptides generated by the same cleaving as in step (a);
(d) labeling the chemically synthesized peptide standards with a second isotope tag, wherein the second isotope tag labels the chemically synthesized peptide standards with an isotopically distinct version of the first isotope tag, thereby generating a plurality of isotopically-labeled chemically synthesized peptide standards;
(e) adding a known absolute amount of a plurality of the isotopically-labeled chemically synthesized peptide standards of known sequences to the isotopically-labeled sample peptides, thereby generating a mixture of isotopically-labeled sample peptides and isotopically-labeled chemically synthesized peptide standards;
(f) resolving the mixture of labeled sample peptides and labeled chemically synthesized peptide standards into a plurality of resolved fractions;
(g) analyzing the resolved fractions by mass spectrometry;
(h) identifying an isotopically-labeled sample peptide in an analyzed fraction from step (g); and
(i) determining the amount of the identified isotopically-labeled sample peptide in the analyzed fraction by comparing the amount of the identified isotopically-labeled sample peptide to the amount of the isotopically-labeled chemically synthesized peptide standard in the analyzed fraction.

16. The method of claim 15, wherein the analyzing by mass spectrometry comprises depositing the plurality of fractions onto a mass spectrometry sample plate.

17. The method of claim 15, wherein the cleaving of the polypeptide sample comprises cleaving with a protease.

18. The method of claim 17, wherein the protease is trypsin.

19. The method of claim 15, wherein the polypeptide sample is obtained from a body fluid selected from the group consisting of blood, plasma, serum, cerebrospinal fluid, urine, saliva, seminal plasma, and pancreatic juice.

20. A method of identifying and quantifying polypeptides in a sample, comprising the steps of:
(a) cleaving a polypeptide sample to generate sample peptides;
(b) labeling the sample peptides with a first isotope tag, to provide a sample of a first isotopically-labeled peptide;
(c) synthesizing a plurality of peptide standards of known sequences by recombinantly expressing the peptide standards, wherein the peptide standards of known sequences comprise sequences of peptides generated by the same cleaving as in step (a);
(d) labeling the peptide standards with a second isotope tag, wherein the second isotope tag labels the peptide standards with an isotopically distinct version of the first isotope tag, thereby generating a plurality of isotopically-labeled peptide standards;
(e) adding a known absolute amount of a plurality of the isotopically-labeled peptide standards of known sequences to the isotopically-labeled sample peptides, thereby generating a mixture of isotopically-labeled sample peptides and isotopically-labeled peptide standards;
(f) resolving the mixture of labeled sample peptides and labeled peptide standards into a plurality of resolved fractions;
(g) analyzing the resolved fractions by mass spectrometry;
(h) identifying an isotopically-labeled sample peptide in an analyzed fraction from step (g); and
(i) determining the amount of the identified isotopically-labeled sample peptide in the analyzed fraction by comparing the amount of the identified isotopically-labeled sample peptide to the amount of the isotopically-labeled peptide standards in the analyzed fraction.

21. The method of claim 20, wherein each of the synthetic peptide standards is recombinantly expressed as a single peptide product.

22. The method of claim 20, wherein each of the synthetic peptide standards is recombinantly expressed as a concatenated peptide product.

23. The method of claim 20, wherein the analyzing by mass spectrometry comprises depositing the plurality of fractions onto a mass spectrometry sample plate.

24. The method of claim 20, wherein the cleaving of the polypeptide sample comprises cleaving with a protease.

25. The method of claim 24, wherein the protease is trypsin.

26. The method of claim 20, wherein the polypeptide sample is obtained from a body fluid selected from the group consisting of blood, plasma, serum, cerebrospinal fluid, urine, saliva, seminal plasma, and pancreatic juice.

27. A method for identifying and quantifying polypeptides in a sample, comprising the steps of:
(a) labeling a polypeptide sample with a first isotope tag to provide a sample of a first isotopically-labeled polypeptide;
(b) cleaving the first isotopically-labeled polypeptide sample to generate isotopically-labeled sample peptides;
(c) chemically synthesizing a plurality of peptide standards of known sequences, wherein the chemically synthesized peptide standards of known sequences comprise sequences of peptides generated by the same cleaving as in step (b);
(d) labeling the chemically synthesized peptide standards with a second isotope tag, wherein the second isotope tag labels the chemically synthesized peptide standards with an isotopically distinct version of the first isotope tag, thereby generating a plurality of isotopically-labeled chemically synthesized peptide standards;
(e) adding the plurality of the isotopically-labeled chemically synthesized peptide standards of known sequences to the isotopically-labeled sample peptides, thereby generating a mixture of isotopically-labeled sample peptides and isotopically-labeled chemically synthesized peptide standards;
(f) resolving the mixture of labeled sample peptides and labeled chemically synthesized peptide standards into a plurality of resolved fractions;
(g) analyzing the resolved fractions by mass spectrometry;
(h) identifying an isotopically-labeled sample peptide in an analyzed fraction from step (g); and
(i) determining the amount of the identified isotopically-labeled sample peptide in the analyzed fraction by comparing the amount of the identified isotopically-labeled sample peptide to the amount of the isotopically-labeled chemically synthesized peptide standard in the analyzed fraction.

28. A method of identifying and quantifying polypeptides in a sample, comprising the steps of:
(a) labeling a polypeptide sample with a first isotope tag to provide a sample of a first isotopically-labeled polypeptide;
(b) cleaving the first isotopically-labeled polypeptide sample to generate isotopically-labeled sample peptides;

(c) synthesizing a plurality of peptide standards of known sequences by recombinantly expressing the peptide standards, wherein the peptide standards of known sequences comprise sequences of peptides generated by the same cleaving as in step (b);

(d) labeling the peptide standards with a second isotope tag, wherein the second isotope tag labels the peptide standards with an isotopically distinct version of the first isotope tag, thereby generating a plurality of isotopically-labeled recombinantly expressed peptide standards;

(e) adding a plurality of the isotopically-labeled peptide standards of known sequences to the isotopically-labeled sample peptides, thereby generating a mixture of isotopically-labeled sample peptides and isotopically-labeled peptide standards;

(f) resolving the mixture of labeled sample peptides and labeled peptide standards into a plurality of resolved fractions;

(g) analyzing the resolved fractions by mass spectrometry;

(h) identifying an isotopically-labeled sample peptide in an analyzed fraction from step (g); and (i) determining the amount of the identified isotopically-labeled sample peptide in the analyzed fraction by comparing the amount of the identified isotopically-labeled sample peptide to the amount of the identified isotopically-labeled peptide standard in the analyzed fraction.

29. A method of identifying and quantifying polypeptides in a sample, comprising the steps of:

(a) labeling a polypeptide sample with a first isotope tag to provide a sample of a first isotopically-labeled polypeptide;

(b) cleaving the first isotopically-labeled polypeptide sample to generate isotopically-labeled sample peptides;

(c) chemically synthesizing a plurality of peptide standards of known sequences, wherein the chemically synthesized peptide standards of known sequences comprise sequences of peptides generated by the same cleaving as in step (b);

(d) labeling the chemically synthesized peptide standards with a second isotope tag, wherein the second isotope tag labels the chemically synthesized peptide standards with an isotopically distinct version of the first isotope tag, thereby generating a plurality of isotopically-labeled chemically synthesized peptide standards;

(e) adding a known absolute amount of a plurality of the isotopically-labeled chemically synthesized peptide standards of known sequences to the isotopically-labeled sample peptides, thereby generating a mixture of isotopically-labeled sample peptides and isotopically-labeled chemically synthesized peptide standards;

(f) resolving the mixture of labeled sample peptides and labeled chemically synthesized peptide standards into a plurality of resolved fractions;

(g) analyzing the resolved fractions by mass spectrometry;

(h) identifying an isotopically-labeled sample peptide in an analyzed fraction from step (g); and (i) determining the amount of the identified isotopically-labeled sample peptide in the analyzed fraction by comparing the amount of the identified isotopically-labeled sample peptide to the amount of the isotopically-labeled chemically synthesized peptide standard in the analyzed fraction.

30. A method of identifying and quantifying polypeptides in a sample, comprising the steps of:

(a) labeling a polypeptide sample with a first isotope tag to provide a sample of a first isotopically-labeled polypeptide;

(b) cleaving the first isotopically-labeled polypeptide sample to generate isotopically-labeled sample peptides;

(c) synthesizing a plurality of peptide standards of known sequences by recombinantly expressing the peptide standards, wherein the peptide standards of known sequences comprise sequences of peptides generated by the same cleaving as in step (b);

(d) labeling the peptide standards with a second isotope tag, wherein the second isotope tag labels the peptide standards with an isotopically distinct version of the first isotope tag, thereby generating a plurality of isotopically-labeled peptide standards;

(e) adding a known absolute amount of a plurality of the isotopically-labeled peptide standards of known sequences to the isotopically-labeled sample peptides, thereby generating a mixture of isotopically-labeled sample peptides and isotopically-labeled peptide standards;

(f) resolving the mixture of labeled sample peptides and labeled peptide standards into a plurality of fractions;

(g) analyzing the resolved fractions by mass spectrometry;

(h) identifying an isotopically-labeled sample peptide in an analyzed fraction from step (g); and (i) determining the amount of the identified isotopically-labeled sample peptide in the analyzed fraction by comparison to the amount of isotopically-labeled peptide standards in the analyzed fraction.

* * * * *

UNITED STATES PATENT AND TRADEMARK OFFICE
CERTIFICATE OF CORRECTION

PATENT NO. : 7,655,433 B2  Page 1 of 1
APPLICATION NO. : 10/455246
DATED : February 2, 2010
INVENTOR(S) : Rudolf H. Aebersold It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 3 days.

Signed and Sealed this

Twenty-third Day of November, 2010

David J. Kappos
*Director of the United States Patent and Trademark Office*